(12) United States Patent
Trinquet et al.

(10) Patent No.: US 8,663,928 B2
(45) Date of Patent: Mar. 4, 2014

(54) METHOD FOR THE DETECTION OF POST-TRANSLATIONAL MODIFICATIONS

(75) Inventors: Eric Trinquet, Point-St-Esprit (FR); Achim Brinker, San Diego, CA (US); Emmanuel Claret, Rochefort Du Gard (FR); Gérard Mathis, Bagnols sur Ceze (FR)

(73) Assignee: CIS BIO International, Gif sur Yvette (FR)

( * ) Notice: Subject to any disclaimer, the term of this patent is extended or adjusted under 35 U.S.C. 154(b) by 969 days.

(21) Appl. No.: 12/516,333

(22) PCT Filed: Nov. 27, 2007

(86) PCT No.: PCT/IB2007/004341
§ 371 (c)(1), (2), (4) Date: May 26, 2009

(87) PCT Pub. No.: WO2008/065540
PCT Pub. Date: Jun. 5, 2008

(65) Prior Publication Data
US 2010/0086943 A1 Apr. 8, 2010

Related U.S. Application Data

(60) Provisional application No. 60/861,085, filed on Nov. 27, 2006.

(51) Int. Cl.
*G01N 33/68* (2006.01)
*G01N 33/53* (2006.01)
*G01N 33/58* (2006.01)

(52) U.S. Cl.
USPC ............................. 435/7.1; 436/86; 436/172

(58) Field of Classification Search
None
See application file for complete search history.

(56) References Cited

U.S. PATENT DOCUMENTS

2003/0059811 A1* 3/2003 Djaballah et al. ................ 435/6

FOREIGN PATENT DOCUMENTS

| WO | WO 00/43780 | * | 7/2000 | ............. G01N 33/50 |
| WO | WO 01/36617 | | 5/2001 | |

OTHER PUBLICATIONS

Adams et al. "Cellular Ser/Thr-Kinase Assays Using Generic Peptide Substrates" Current Chemical Genomics, 2008, 1, 54-64, published online May 23, 2008.*

Chambon et al. ("Screening and profiling for kinases: development of a unique and versatile platform", May 2005, Miptec 2005, Basel, Switzerland, retrieved from http://www.htrf.com/sites/default/files/ressources/Poster_Chambon_miptec2005_Kinasetoolbox.pdf on Jun. 27, 2012.*

Nagamune et al. "Bioimaging of Phosphorylation of Erk1 in Living Cell Using Fluorescence Resonance Energy Transfer", Abstract No. 1553, 2006 Annual Meeting US—Japan Joint Topical Conference on Medical Engineering, Drug Delivery Systems and Therapeutic Systems, Nov. 13, 2006, http://apps.aiche.org/Proceedings/Abstract.aspx?PaperID=62440, 2 pgs.*

Osmond et al. "GPCR Screening via ERK A Novel Platform for Screening G Protein—Coupled Receptors" Journal of Biomolecular Screening 10(7); 2005, published online Aug. 29, 2005.*

Ni, Qiang et al., "Analyzing protein kinase dynamics in living cells with FRET reporters," ScienceDirect, vol. 40, pp. 279-286, (2006).

Gautier, M. et al., "Homo-FRET Microscopy in Living Cells to Measure Monomer-Dimer Trasition of GFP-Tagged Proteins," Biophysical Journal, vol. 80, pp. 3000-3008, (Jun. 2001).

International Search Report for PCT/IB2007/004341, dated Aug. 4, 2008.

Written Opinion for PCT/IB2007/004341, dated Aug. 4, 2008.

* cited by examiner

*Primary Examiner* — Christine Foster
(74) *Attorney, Agent, or Firm* — Hunton & Williams LLP

(57) ABSTRACT

Method for the detection in homogeneous medium of a post-translational modification of a proteinaceous substrate catalyzed by a cell enzyme, characterized in that the post-translational modification reaction takes place in intact living cells, in that these cells comprise a heterologous expression vector coding for a fusion protein comprising the proteinaceous substrate and a first coupling domain and in that it comprises the following stages:

(i) Incubation of the cells in the presence or in the absence of a compound to be tested capable of modulating the activity of said enzyme, (ii) Addition to the reaction medium of a first fluorescent compound member of a first pair of FRET partners covalently bonded to a coupling agent capable of binding specifically to the first coupling domain present on the proteinaceous substrate, (iii) Addition to the reaction medium of a second fluorescent compound member of this first pair of FRET partners, and covalently bonded to a binding domain specific to the site of the proteinaceous substrate having undergone the post-translational modification and not binding to the non-modified proteinaceous substrate, (i) Measurement of the FRET signal emitted by the sample, this signal being representative of the quantity of proteinaceous substrate having undergone said post-translational modification;

and cells for the implementation of said method.

16 Claims, 14 Drawing Sheets

PTM = post-translational modification
E1 = 1st coupling domain

Reading of Well 1:

Reading of Well 2:

E 1 = 1st coupling domain

E 2 = 2nd coupling domain

PTM = Post-translational Modification

1st pair of FRET partners = A/D1

2nd pair of FRET partner = A/D

Polypeptide = protein substrate

Reading of Well 1:

Reading of Well 2:

E1 = 1st coupling domain

E2 = 2nd coupling domain

PTM = Post-translational modification

1st pair of FRET partners = A/D1

2nd pair of FRET partners = A/D

Polypeptide = protein substrate

Reading 1 Well 1:

Reading 2 Well 1:

SEQUENCE LISTING

```
<160> NUMBER OF SEQ ID NOS: 42

<210> SEQ ID NO 1
<211> LENGTH: 102
<212> TYPE: DNA
<213> ORGANISM: Artificial Sequence
<220> FEATURE:
<223> OTHER INFORMATION: Sense strand coding for a fusion protein

<400> SEQUENCE: 1
gatccgaaca aaaactcatc tcagaagagg atctgaagaa gctcaatcgt acgctgagct      60
tcgcagagcc tggcgactac aaggacgacg atgacaagta gc                        102

<210> SEQ ID NO 2
<211> LENGTH: 102
<212> TYPE: DNA
<213> ORGANISM: Artificial Sequence
<220> FEATURE:
<223> OTHER INFORMATION: Antisense strand

<400> SEQUENCE: 2
tcgagctact tgtcatcgtc gtccttgtag tcgccaggct ctgcgaagtc cagcgtacga      60
ttgagcttct tcagatcctc ttctgagatg agttttttgtt cg                       102

<210> SEQ ID NO 3
<211> LENGTH: 8
<212> TYPE: PRT
<213> ORGANISM: Artificial Sequence
<220> FEATURE:
<223> OTHER INFORMATION: FLAG peptide

<400> SEQUENCE: 3

Asp Tyr Lys Asp Asp Asp Asp Lys
1               5

<210> SEQ ID NO 4
<211> LENGTH: 10
<212> TYPE: PRT
<213> ORGANISM: Homo sapiens

<400> SEQUENCE: 4
```

Glu Gln Lys Leu Ile Ser Glu Glu Asp Leu
1               5                   10

<210> SEQ ID NO 5
<211> LENGTH: 9
<212> TYPE: PRT
<213> ORGANISM: Influenza virus
<220> FEATURE:
<221> NAME/KEY: MISC_FEATURE
<222> LOCATION: (1)..(9)
<223> OTHER INFORMATION: Influenza hemaglutinin epitope

<400> SEQUENCE: 5

Tyr Pro Tyr Asp Val Pro Asp Tyr Ala
1               5

<210> SEQ ID NO 6
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Domain of guanine nucleotide binding protein
      beta-3
<300> PUBLICATION INFORMATION:
<308> DATABASE ACCESSION NUMBER: Genebank NP-002066
<309> DATABASE ENTRY DATE: 2012-03-24
<313> RELEVANT RESIDUES IN SEQ ID NO: (1)..(19)

<400> SEQUENCE: 6

Cys Ser Ile Tyr Asn Leu Lys Ser Arg Glu Gly Asn Val Lys Val Ser
1               5                   10                  15

Arg Glu Leu

<210> SEQ ID NO 7
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Mono ADP ribolsylation site protein Galphai3

<400> SEQUENCE: 7

Phe Asp Arg Val Thr Asp Val Ile Ile Lys Asn Asn Leu Lys Glu Cys
1               5                   10                  15

Gly Leu Tyr

<210> SEQ ID NO 8
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: Mono ADP ribolsylation site Ras related protein
      RAP1B
<300> PUBLICATION INFORMATION:
<308> DATABASE ACCESSION NUMBER: NP-056461
<309> DATABASE ENTRY DATE: 2012-04-01
<313> RELEVANT RESIDUES IN SEQ ID NO: (1)..(18)

<400> SEQUENCE: 8

Lys Tyr Asp Pro Thr Ile Glu Asp Ser Tyr Arg Lys Gln Val Glu Val
1               5                   10                  15

Asp Ala

-continued

```
<210> SEQ ID NO 9
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Acetylation site p53

<400> SEQUENCE: 9

Glu Trp Tyr Lys Lys Met Leu Asp Lys Ala Val Ser Glu Arg Ile Val
1               5                   10                  15

<210> SEQ ID NO 10
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Acetylation site HMG14
<300> PUBLICATION INFORMATION:
<308> DATABASE ACCESSION NUMBER: NP-004956
<309> DATABASE ENTRY DATE: 2012-03-24
<313> RELEVANT RESIDUES IN SEQ ID NO: (1)..(10)

<400> SEQUENCE: 10

Ser Ala Glu Gly Ala Ala Lys Glu Glu Pro
1               5                   10

<210> SEQ ID NO 11
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: O-glycosylation site microfibrillar associated
      protein 2
<300> PUBLICATION INFORMATION:
<308> DATABASE ACCESSION NUMBER: NP-059453
<309> DATABASE ENTRY DATE: 2012-03-26
<313> RELEVANT RESIDUES IN SEQ ID NO: (1)..(11)

<400> SEQUENCE: 11

Pro Asp Tyr Tyr Asp Tyr Gln Glu Val Thr Pro Arg Pro Ser Glu Glu
1               5                   10                  15

<210> SEQ ID NO 12
<211> LENGTH: 19
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: O-glycosylation site c-myc
<300> PUBLICATION INFORMATION:
<308> DATABASE ACCESSION NUMBER: NP-002458
<309> DATABASE ENTRY DATE: 2012-03-31
<313> RELEVANT RESIDUES IN SEQ ID NO: (1)..(19)

<400> SEQUENCE: 12

Lys Phe Glu Leu Leu Pro Thr Pro Pro Leu Ser Pro Ser Arg Arg Ser
1               5                   10                  15

Gly Leu Cys

<210> SEQ ID NO 13
<211> LENGTH: 17
<212> TYPE: PRT
<213> ORGANISM: Homo sapiens
```

```
<220> FEATURE:
<221> NAME/KEY: MISC_FEATURE
<222> LOCATION: (1)..(17)
<223> OTHER INFORMATION: N-glycosylation site b chain of IL6 receptor
<300> PUBLICATION INFORMATION:
<308> DATABASE ACCESSION NUMBER: NP-002175
<309> DATABASE ENTRY DATE: 2012-04-01
<313> RELEVANT RESIDUES IN SEQ ID NO: (1)..(17)

<400> SEQUENCE: 13

Ile Glu Ser Pro Trp Gln Leu His Ser Asn Phe Thr Ala Val Cys Val
1               5                   10                  15

Leu

<210> SEQ ID NO 14
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: N-glycosylation site insulin receptor
<300> PUBLICATION INFORMATION:
<308> DATABASE ACCESSION NUMBER: NP-000199
<309> DATABASE ENTRY DATE: 2012-04-01
<313> RELEVANT RESIDUES IN SEQ ID NO: (1)..(18)

<400> SEQUENCE: 14

Val Cys Pro Gly Met Asp Ile Arg Asn Asn Leu Thr Arg Leu His Glu
1               5                   10                  15

Leu Glu

<210> SEQ ID NO 15
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Methylation site fibroblast growth factor
<300> PUBLICATION INFORMATION:
<308> DATABASE ACCESSION NUMBER: NP-000199
<309> DATABASE ENTRY DATE: 2012-04-01
<313> RELEVANT RESIDUES IN SEQ ID NO: (1)..(17)

<400> SEQUENCE: 15

Arg Gly Arg Ala Leu Pro Gly Gly Arg Leu Gly Gly Arg Gly Arg Gly
1               5                   10                  15

Arg

<210> SEQ ID NO 16
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: methylation site small nuclear
      ribonucleoprotein polypeptide D3 domain
<300> PUBLICATION INFORMATION:
<308> DATABASE ACCESSION NUMBER: NP-004166
<309> DATABASE ENTRY DATE: 1999-12-12
<313> RELEVANT RESIDUES IN SEQ ID NO: (1)..(17)

<400> SEQUENCE: 16

Ala Ile Leu Lys Ala Gln Val Ala Ala Arg Gly Arg Gly Arg Gly Met
1               5                   10                  15

Gly
```

```
<210> SEQ ID NO 17
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Phosphorylation site recognized by cyclin
      dependent kinase
<220> FEATURE:
<221> NAME/KEY: VARIANT
<222> LOCATION: (1)..(1)
<223> OTHER INFORMATION: Xaa can be Ser or Thr
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be Lys or Arg

<400> SEQUENCE: 17

Xaa Pro Xaa Xaa
1

<210> SEQ ID NO 18
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: phosphorylation site recognized by casein
      kinase I

<400> SEQUENCE: 18

Ser Glu Phe Asp Thr Gly Ser Ile Ile Ile Phe Phe
1               5                   10

<210> SEQ ID NO 19
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Phosphorylation site recognized by casein
      kinase II

<400> SEQUENCE: 19

Glu Asp Glu Glu Ser Glu Asp Glu Glu
1               5

<210> SEQ ID NO 20
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Phosphorylation site recognized by camK II

<400> SEQUENCE: 20

Lys Arg Gln Gln Ser Phe Asp Leu Phe
1               5

<210> SEQ ID NO 21
<211> LENGTH: 9
<212> TYPE: PRT
<213> ORGANISM: Homo sapiens
```

```
<220> FEATURE:
<221> NAME/KEY: MISC_FEATURE
<222> LOCATION: (1)..(9)
<223> OTHER INFORMATION: Phosphorylation site Erk 1/2 domain

<400> SEQUENCE: 21

Val Thr Pro Arg Thr Pro Pro Pro Ser
1               5

<210> SEQ ID NO 22
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Phosphorylation site Akt domain

<400> SEQUENCE: 22

Gly Arg Pro Arg Thr Ser Ser Phe Ala Glu Gly
1               5                   10

<210> SEQ ID NO 23
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Phosphorylation site PKA domain
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be Ser or Thr

<400> SEQUENCE: 23

Arg Arg Xaa Xaa
1

<210> SEQ ID NO 24
<211> LENGTH: 9
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa can be any amino acid

<400> SEQUENCE: 24

Ala Xaa Val Ile Tyr Ala Ala Pro Phe
1               5

<210> SEQ ID NO 25
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Phosphorylation site EGFR domain

<400> SEQUENCE: 25

Glu Glu Glu Glu Tyr Phe Glu Leu Val
1               5

<210> SEQ ID NO 26
```

```
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa can be any amino acid
<220> FEATURE:
<221> NAME/KEY: MISC_FEATURE
<222> LOCATION: (1)..(9)
<223> OTHER INFORMATION: Phosphorylation site Lck domain
<220> FEATURE:
<221> NAME/KEY: VARIANT
<222> LOCATION: (3)..(3)
<223> OTHER INFORMATION: Xaa can be any amino acid

<400> SEQUENCE: 26

Xaa Glu Xaa Ile Tyr Gly Val Leu Phe
1               5

<210> SEQ ID NO 27
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Prenylation site RAB3
<300> PUBLICATION INFORMATION:
<308> DATABASE ACCESSION NUMBER: NP-002857
<309> DATABASE ENTRY DATE: 1999-12-12
<313> RELEVANT RESIDUES IN SEQ ID NO: (1)..(16)

<400> SEQUENCE: 27

Pro Gln Leu Ser Asp Gln Gln Val Pro Pro His Gln Asp Cys Ala Cys
1               5                   10                  15

<210> SEQ ID NO 28
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Prenylation site Heat shock 40kDa protein
<300> PUBLICATION INFORMATION:
<308> DATABASE ACCESSION NUMBER: NP-001530
<309> DATABASE ENTRY DATE: 1999-12-25
<313> RELEVANT RESIDUES IN SEQ ID NO: (1)..(17)

<400> SEQUENCE: 28

Tyr Glu Asp Asp Glu His His Pro Arg Gly Gly Val Gln Cys Gln Thr
1               5                   10                  15

Ser

<210> SEQ ID NO 29
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: Sumoylation site PML
<300> PUBLICATION INFORMATION:
<308> DATABASE ACCESSION NUMBER: NP-150241
<309> DATABASE ENTRY DATE: 1999-12-25
<313> RELEVANT RESIDUES IN SEQ ID NO: (1)..(18)

<400> SEQUENCE: 29

Cys Phe Glu Ala His Gln Trp Phe Leu Lys His Glu Ala Arg Pro Leu
1               5                   10                  15
```

Ala Glu

<210> SEQ ID NO 30
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Sumoylation site DNA topoisomerase I
<300> PUBLICATION INFORMATION:
<308> DATABASE ACCESSION NUMBER: NP-003277
<309> DATABASE ENTRY DATE: 1999-12-25
<313> RELEVANT RESIDUES IN SEQ ID NO: (1)..(17)

<400> SEQUENCE: 30

Lys Lys Glu Lys Glu Asn Gly Ser Ser Pro Pro Gln Ile Lys Asp Glu
1               5                   10                  15

Pro

<210> SEQ ID NO 31
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Ubiquitination site IkBa
<300> PUBLICATION INFORMATION:
<308> DATABASE ACCESSION NUMBER: NP-065390
<309> DATABASE ENTRY DATE: 1999-12-25
<313> RELEVANT RESIDUES IN SEQ ID NO: (1)..(17)

<400> SEQUENCE: 31

Glu Gly Pro Arg Asp Gly Leu Lys Lys Glu Arg Leu Leu Asp Asp Arg
1               5                   10                  15

His

<210> SEQ ID NO 32
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Ubiquitination site CDC25C
<300> PUBLICATION INFORMATION:
<308> DATABASE ACCESSION NUMBER: NP-001781
<309> DATABASE ENTRY DATE: 1999-12-25
<313> RELEVANT RESIDUES IN SEQ ID NO: (1)..(17)

<400> SEQUENCE: 32

Met Cys Ser Ser Ser Ala Asn Lys Glu Asn Asp Asn Gly Asn Leu Val
1               5                   10                  15

Asp

<210> SEQ ID NO 33
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Proteolysis site recognized by the Caspases
      1, 4, 5
<220> FEATURE:
<221> NAME/KEY: VARIANT
<222> LOCATION: (1)..(1)
<223> OTHER INFORMATION: Xaa can be Trp or Leu
<220> FEATURE:

```
<221> NAME/KEY: VARIANT
<222> LOCATION: (5)..(5)
<223> OTHER INFORMATION: Xaa can be any amino acid

<400> SEQUENCE: 33

Xaa Glu His Asp Xaa
1               5

<210> SEQ ID NO 34
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Proteolysis site recognized by the Caspases
      2, 3, 7
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (5)..(5)
<223> OTHER INFORMATION: Xaa can be any amino acid

<400> SEQUENCE: 34

Asp Glu Xaa Asp Xaa
1               5

<210> SEQ ID NO 35
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Proteolysis site recognized by the Caspases
      6, 8, 9
<220> FEATURE:
<221> NAME/KEY: MISC_FEATURE
<222> LOCATION: (1)..(1)
<223> OTHER INFORMATION: Xaa can be Ile, Leu, or Val
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 35

Xaa Val Glu Asp Xaa
1               5

<210> SEQ ID NO 36
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Proteolysis site recognized by the complement
      C1r
<220> FEATURE:
<221> NAME/KEY: VARIANT
<222> LOCATION: (8)..(8)
<223> OTHER INFORMATION: Xaa can be any amino acid

<400> SEQUENCE: 36

Pro Phe Glu Glu Lys Gln Arg Xaa
1               5
```

```
<210> SEQ ID NO 37
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Prenylation site sequence recongnized by
      farnesyltransferase and geranylgeranyltransferase
<220> FEATURE:
<221> NAME/KEY: VARIANT
<222> LOCATION: (4)..(4)
<223> OTHER INFORMATION: Xaa can be any amino acid

<400> SEQUENCE: 37

Cys Ala Ala Xaa
1

<210> SEQ ID NO 38
<211> LENGTH: 5
<212> TYPE: PRT
<213> ORGANISM: Homo sapiens
<220> FEATURE:
<221> NAME/KEY: VARIANT
<222> LOCATION: (1)..(3)
<223> OTHER INFORMATION: Xaa can be any amino acid

<400> SEQUENCE: 38

Xaa Xaa Xaa Cys Cys
1               5

<210> SEQ ID NO 39
<211> LENGTH: 5
<212> TYPE: PRT
<213> ORGANISM: Homo sapiens
<220> FEATURE:
<221> NAME/KEY: VARIANT
<222> LOCATION: (1)..(2)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be any amino acid

<400> SEQUENCE: 39

Xaa Xaa Cys Xaa Cys
1               5

<210> SEQ ID NO 40
<211> LENGTH: 5
<212> TYPE: PRT
<213> ORGANISM: Homo sapiens
<220> FEATURE:
<221> NAME/KEY: VARIANT
<222> LOCATION: (1)..(2)
<223> OTHER INFORMATION: Xaa can be any amino acid
<220> FEATURE:
<221> NAME/KEY: VARIANT
<222> LOCATION: (5)..(5)
<223> OTHER INFORMATION: Xaa can be any amino acid

<400> SEQUENCE: 40

Xaa Xaa Cys Cys Xaa
1               5

<210> SEQ ID NO 41
<211> LENGTH: 5
<212> TYPE: PRT
<213> ORGANISM: Homo sapiens
<220> FEATURE:
```

```
<221> NAME/KEY: VARIANT
<222> LOCATION: (1)..(1)
<223> OTHER INFORMATION: Xaa can be any amino acid
<220> FEATURE:
<221> NAME/KEY: VARIANT
<222> LOCATION: (4)..(5)
<223> OTHER INFORMATION: Xaa can be any amino acid

<400> SEQUENCE: 41

Xaa Cys Cys Xaa Xaa
1               5

<210> SEQ ID NO 42
<211> LENGTH: 5
<212> TYPE: PRT
<213> ORGANISM: Homo sapiens
<220> FEATURE:
<221> NAME/KEY: VARIANT
<222> LOCATION: (3)..(5)
<223> OTHER INFORMATION: Xaa can be any amino acid

<400> SEQUENCE: 42

Cys Cys Xaa Xaa Xaa
1               5
```

METHOD FOR THE DETECTION OF POST-TRANSLATIONAL MODIFICATIONS

CROSS-REFERENCE TO RELATED APPLICATIONS

This application is the U.S. National Stage filing of International Application No. PCT/IB2007/004341, filed Nov. 27, 2007, which claims priority to U.S. Provisional Patent Application No. 60/861,085, filed Nov. 27, 2006, the disclosures of which are hereby incorporated in their entirety by reference.

TECHNICAL FIELD

The present invention relates to methods and tools making it possible to measure post-translational modifications of peptides or proteins in a cell environment.

STATE OF THE PRIOR ART

Advances in cell and molecular biology are making it possible to study cell processes in a very detailed manner: thanks to molecular biology, it is now possible to isolate the molecules involved in a given cell process, study their interactions and their modes of operation in vitro. These techniques make it possible to test the effect of compounds capable of becoming future medicaments on signalling paths and protein targets potentially involved in diseases.

One of the key stages in research into new biologically active compounds thus involves bringing them into contact with a cell, and determining whether or not these compounds have an effect on this cell. For this purpose, the effect of these compounds on a mechanism for translation of a given signal is generally studied. In a schematic manner, it can be considered that a biologically active compound will bind to a molecule involved in a cell mechanism, and will modify its behaviour: such compounds can therefore be detected either by measuring their binding to said molecule involved in a cell mechanism, or by measuring the activation or the inhibition of the considered cell mechanism, in the presence or absence of the compound to be tested.

It is known that the mechanisms for translation of the signal in particular involve enzymes which will modify proteins in the cell. These modifications of the cell proteins are called post-translational modifications and involve the modification of the skeletal structure of the polypeptide originating from the ribosomal translation by adding or cutting chemical groups, changing the three-dimensional structure or cutting the protein chain. Such modifications include the addition of phosphate (phosphorylation), ADP ribosyl (ADP-ribosylation), a methyl (methylation) or acetyl (acetylation) group, carbohydrate (glycosylation), fatty acid (prenylation), ubiquitin (ubiquitination), SUMO (Sumoylation) or proteolytic cutting of the protein (proteolysis). Additional examples of post-translational modifications include hydroxylation, myristoylation, palmitylation, neddylation, iodation, sulphation. A certain number of post-translational modifications do not involve enzymes: this is the case with nitration and glutathionylation.

These post-translational modifications are key elements which make it possible to modulate the function of the proteins and hence their role in the cell mechanisms. These post-translational modifications affect the majority of the eukaryotic proteins. They make it possible for the cell, starting from a single gene, to produce several effectors depending on the modifications made to the protein skeletal structure. The post-translational modifications determine the state of activation of an enzyme or of a protein, its intracellular location and/or its excretion, the interactions that it can have its stability and its degradation. These mechanisms are very finely regulated, since they allow the cell to modify its behaviour and adapt to its environment. Frequently, the deregulation of one or more effectors responsible for the post-translational modifications leads to pathological states of the organism.

For these reasons the enzymes involved in the mechanisms of post-translational modifications represent major targets for the pharmaceutical industry. The availability of tools making it possible to study the post-translational modifications undergone by a target polypeptide under cell conditions therefore represents a particularly important consideration for research into new medicaments.

Most of the studies relating to the modulation of the post-translational modifications are carried out using biochemical assays based on the use of recombinant enzymes, purified from insect or mammal cell cultures. The technique most often described for the study of the modifications involving a transfer of a donor compound group to a polypeptide substrate, consists, in a first phase, in mixing the enzyme catalyzing the post-translational modification, the donor compound and the polypeptide acceptor of the post-translational modification. In a second phase, a specific probe (i.e. capable of distinguishing the modified polypeptide from the non-modified polypeptide) is added to the mixture. This approach is very widely used in the field of potential drug screening. The methods differ mainly in the method for the detection and/or the technology which makes it possible to demonstrate the fixing/binding of the specific probe to the modified polypeptide.

Other methods first cause the compound to be tested to act on living cells. After lysis of the cells and addition of the appropriate cofactors, the enzymatic activity is tested on a target polypeptide added to the measurement medium.

The biochemical assays of the prior art do not make it possible to study the processes of post-translational modification under conditions close to physiological intracellular conditions.

These assays in fact require the addition to the measurement medium of a certain number of cofactors and group donor compounds (in the case of post-translational modifications consisting of a group transfer), the concentrations of which are different from those encountered in the cell under physiological conditions, which can modify the activity of the enzyme catalyzing the post-translational modification. Moreover, the presence in the measurement medium of high concentrations of group donor compounds prevents the detection of inhibitor compounds acting by competition mechanisms.

Moreover, in these assays, the enzyme added to the measurement medium is in general totally active, which is often very far from the physiological reality. In fact, within the cell only a part of the enzyme molecules are activated, or there are even different populations of molecules activated to different degrees. The biochemical assays of the prior art do not make it possible to work on these different populations in that they are not implemented under physiological conditions. For the same reason, they no longer make it possible to identify allosteric modulators of these enzymes.

Finally, certain compounds to be tested can seem to modulate the post-translational modification reactions when they are identified by the biochemical techniques of the prior art since they have, in fact, no effect under physiological conditions, either because they do not cross the plasma membrane because they are sequestered in a cell compartment, or because they are degraded by the cell. These same techniques can also lead to interest in compounds which ultimately prove toxic when they are used on living cells.

Several technological approaches now exist which make it possible to study and quantify the post-translational modifications involved in living cells, among which there can be mentioned:

The in vivo labelling of the target proteins of the post-translational modification. This approach involves providing the cells with a co-factor carrying a group which will be transferred to the target protein, this group being radiolabelled or more generally marked with a label such as, for example, ADP, Acetyl, GlcNAc, Methyl, Phosphate, Farnesyl, Geranyl, Ubiquitin, SUMO. This leads to a labelling of the target proteins. The modified proteins are then analyzed by electrophoresis or chromatography and autoradiography. The specificity of this approach can be increased either by immunoblotting (Western blot), or by including an immunoprecipitation prior to the electrophoresis. Moreover two-dimensional electrophoresis improves the discrimination between the proteins by separating them not only according to criteria of molecular weight but also by charge.

Mass spectrometry makes it possible to separate protein fragments according to their mass and their charge, from a complex mixture. A post-translational modification increases the mass of a protein sequence. For example: +80 Da for a phosphorylation, +42 Da for an acetylation, +14 Da for a methylation, +204 Da for a farnesylation, +>800 Da for an N-bonded glycosylation, +203 Da or +>800 Da for an O-bonded glycosylation, +1 kDa for a ubiquitination. This technology does not require previous labelling of the target proteins. However the complex mixture of proteins must be fragmented by proteolytic digestion (in general tryptic) before analysis. In order to improve the sensitivity, the study by mass spectrometry is often preceded by an enrichment of the modified proteins, using probes specific to post-translational modification. The analysis is also sometimes preceded by an electrophoretic separation or microcapillary high pressure liquid chromatography (pHPLC).

An improvement to this approach makes it possible to quantify the different protein fragments contained in a complex mixture. Two protein mixtures, originating from the same cells taken in different states, are labelled using biochemical probes. One of the probes is synthesized with light isotopes of the atoms, the other with heavy isotopes. After labelling, the samples are mixed, then fragmented with trypsin, and enriched on an affinity column. The analysis is then carried out by separating the fragments by mass spectrometry. The quantity of a fragment can thus be compared according to the different states of the cell.

The specific recognition of the modified protein by a specific probe (i.e. capable of distinguishing the modified protein from the non-modified protein) (antibody, lectin, specific protein etc.). Numerous techniques are based on the use of antibodies for detecting and quantifying the post-translational modifications.

1) Western blot, which involves the specific recognition of the protein when the latter is immobilized on a membrane. The complex mixture of proteins is in general previously separated by electrophoresis (separation according to mass for one-dimensional electrophoresis, separation according to mass and charge for two-dimensional electrophoresis) before being transferred to the membrane. The modified protein is detected by a probe specific to post-translational modification previously coupled with a development system (for example an enzyme, a fluorochrome).

Developments of this method have been described recently and involve immobilizing cells in a plastic phase, fixing them and permeabilizing them, in order to allow the specific probe to pass through the cell membranes. Then the modified protein is detected by an antibody conjugated to an enzyme, or a fluorochrome. The use of different probes coupled with fluorochromes emitting at different wavelengths makes it possible to measure several post-translational modifications on the same cell sample (Chen H et al. Anal. Biochem. 2005, 338: 136-142).

2) Patent Application WO 2006/017549 A2 describes a method for the analysis of the phosphorylation of the proteins by flow cytometry. After fixing and permeabilization, the cells are incubated with phosphospecific antibodies coupled with fluorochromes. Following washing to remove the excess of non-fixed/non-bound antibodies, the cells are analyzed with a flow cytometer.

3) The ELISA ("Enzyme-Linked Immunosorbant Assay") technique has emerged as a method of choice for the analysis of post-translational modifications. This heterogeneous assay technique is based on the capture of the protein of interest by a first antibody, this antibody being immobilized on a solid phase. The protein is then recognized by a second antibody specific to the post-translational modification. This second antibody is coupled with an enzyme (peroxidase, alkaline phosphatase, β galactosidase, acetylcholine esterase) capable of producing a chromogenic or photochemical reaction, or to a fluorophore (or fluorescent compound). The intensity of the signal (colorimetric, photochemical, fluorescent) being proportional to the quantity of fixed/bound antibody, the ELISA technique makes it possible to quantify the modified protein.

4) Numerous techniques use the same basic principle as ELISA in order to detect the post-translational modifications of the proteins: fixing/binding of the protein by a first antibody, specific recognition of the modified protein by a second antibody. However they differ in the detection technology used, which in certain cases makes it possible to:

5)

analyze several post-translational modifications on the same sample (multiplex assay): this is the case with the techniques known by the trade names: "SEARCH LIGHT" marketed by Endogen (Pierce), "MULTI SPOT" marketed by Meso Scale Discovery, which allow a multiplex assay by means of a different spatial location for each analyte to be detected, or "BEADLYTE" marketed by Upstate (Millipore) which allows the multiplex assay by means of different-coloured beads for each analyte.

measure the phosphorylation of a protein in homogeneous phase. TGR BioSciences markets an assay kit under the name "SUREFIRE" making it possible to measure the phosphorylation of the proteins Erk1 and Erk2.

U.S. Pat. No. 6,335,201 discloses a technique which allows the analysis of post-translational modifications at unicellular level. The cells are microinjected with a protein substrate capable of undergoing the studied post-translational modification. This substrate is coupled with a fluorescent compound beforehand. After lysis of the cell, the modified protein substrate is separated from the non-modified substrate by capillary electrophoresis. The modified and non-modified protein substrates are detected by means of their previous coupling with the fluorescent compound.

Ng T et al. (Science 1999, 283: 2085-2089) describe the microinjection of phosphospecific antibodies labelled with a fluorescent compound in cells previously transfected with protein kinase C(PKC) fused to GFP (Green Fluorescent Protein). Following the phosphorylation of the PKC, the phosphospecific antibodies bind to the PKC, causing the fluorescent compound and the GFP to move closer together. The authors follow, at unicellular level, the reduction in the fluorescence lifetime of the GFP, due to the establishment of an FRET (Fluorescence Resonance Energy Transfer) between the GFP and the fluorescent compound.

Approaches using biological probes have been described recently for studying the post-translational modifications of a target substrate in living cells.

U.S. Pat. No. 6,900,304 describes the use of chimeric proteins making it possible to measure the degree of phosphorylation of a substrate. The chimeric protein is constituted by a donor compound, a phosphorylable domain, a domain recognizing the phosphorylated amino acids and an acceptor compound. Following a phosphorylation, the spatial resolution of the phosphorylable domain and the domain recognizing the phosphorylated amino acids leads to a bringing together of donor compound and acceptor compound.

Hideyoshi H et al. (FEBS Lett. 1997, 414: 55-60) describe the use of peptides coupled with 6-acryloyl-2-dimethlaminonaphthalene (Acrylodan) or N-(7-dimethylamino-4-methylcoumarinyl) maleimide (DACM) which are permeable at the cell membrane. In the intracellular medium, the phosphorylation of the peptides is followed by measuring the reduction in the fluorescence emitted at 524 nm (acrylodan) or at 475 nm (DACM) after excitation of the fluorophores.

Finally, Wouters et al. (Current Biology, 1999, 9:1127-1130, describe a method making it possible to measure the phosphorylation of the EGFR receptor: this receptor is expressed in the form of a fusion protein with green fluorescent protein (GFP). In the presence of antibodies specific to phosphotyrosine and conjugated to cyanine 3 (Cy-3), a FRET takes place between the GFP and Cy-3, and this FRET is measured by the "FLIM" technique (Fluorescence Lifetime Imaging Microscopy). These techniques making it possible to study the processes of post-translational modification under intracellular conditions suffer from a certain number of limitations in their implementation:

they require steps of separation/detection which are tedious to implement and not applicable to screening at high flow rates of compounds capable of modulating the mechanisms of post-translational modifications, the techniques requiring the addition to the measurement medium of large quantities of group donor compound (in the case of group transfer reactions) do not make it possible to detect the compounds modulating these modifications by competition mechanisms with the group donor compounds, the majority of these techniques detect only the quantity of protein having undergone a post-translational modification without taking into account the total quantity of protein to be modified present in the cell or the cell pool studied. This quantity being able to vary significantly from one sample to the other or from one reaction well to the other in the implementation of screening at high flow rates. It can be particularly useful to standardize the measurement of the post-translational-modification process by calculating a "quantity of modified protein/quantity of total protein" ratio.

A need therefore exists for a technique making it possible to study the post-translational modifications under the conditions closest to the natural cell environment, requiring a minimum of stages and, in particular, not using the tedious methods of separation and/or detection described in the prior art.

DISCLOSURE OF THE INVENTION

Definitions

"Post-translational modification": this term designates a chemical modification of a protein taking place after its translation, comprising the reactions of group transfer to, or starting from, the protein or reactions of proteolysis. The following reactions are post-translational modification reactions: Mono ADP ribosylation; Poly ADP ribosylation; Acetylation; Glutathionylation; O-Glycosylation; N-Glycosylation; Methylation; Nitration; Phosphorylation; prenylation; Sumoylation; Ubiquitination; Proteolysis; Biotinylation; Glutamylation.

"Coupling domain/Coupling agent": these terms designate a pair of compounds capable of establishing between them a covalent or non-covalent bond with high affinity in the cell. The Coupling domain/Coupling agent pairs can be constituted by the following pairs: peptide sequence/antibodies specific to this peptide sequence, "Tag"/anti-tag antibodies, suicide enzyme/suicide enzyme substrate, biotin/avidin.

The Coupling domain/Coupling agent pairs are used in the invention for coupling a fluorescent compound with a protein substrate present in the cell, in other words for labelling a protein substrate with this fluorescent compound.

"Measurement medium": this term designates the container in which the test is carried out. It can be, for example, a microplate well or a cell incubation chamber.

"Intact living cell": this expression designates living cells the membrane and intracellular integrity of which is preserved. Cells containing one or more vector(s) for heterologous expression are intact living cells within the meaning of the invention.

"Method in homogeneous medium": method carried out in a liquid medium, in the absence of a solid phase.

"Permeabilization": within the meaning of the invention, the permeabilization of cells comprises any treatment applied to a cell making it possible for compounds not permeable to the plasma membrane to enter the cell. The lysis of cells is included in this definition.

"Energy transfer between fluorescent molecules" or "Energy transfer by Forster type resonance" or "FRET" (for "Fluorescence Resonance Energy Transfer" or more strictly speaking "Forster Resonance Energy Transfer"): designates a quantum phenomenon being produced between two fluorescent molecules close to one another (distance comprised between ten and one hundred Angstrom) and the emission spectrum of one of which (the fluorescent donor compound) partially covers the excitation spectrum of the other (the fluorescent acceptor compound). When the fluorescent donor compound is excited by a photon, it can transmit its energy to the fluorescent acceptor compound which is then in an excited state and emits light.

"Pair of FRET partners": this expression designates a pair constituted by a fluorescent donor compound and a fluorescent acceptor compound capable, when they are in proximity to one another and when they are excited at the excitation wavelength of the fluorescent donor compound, of emitting a FRET signal. It is known that in order for two fluorescent compounds to be FRET partners, the emission spectrum of the fluorescent donor compound must partially cover the excitation spectrum of the fluorescent acceptor compound.

"FRET signal": designates any measurable signal representing a FRET between a fluorescent donor compound and a fluorescent acceptor compound. A FRET signal can therefore be a variation in the intensity or fluorescence lifetime of the fluorescent donor compound or the fluorescent acceptor compound.

The method for the detection of post-translational modifications according to the invention involves detecting by the FRET technique a protein or peptide substrate having undergone a post-translational modification in a functional living cell. Thus, with the exception of the protein substrate undergoing the post-translational modification, and optionally of the enzyme catalyzing this reaction, which are overexpressed in the cell, the method according to the invention does not require the addition of any co-factor involved in the reaction (for example the addition of high concentrations of ATP for the kinase assays), nor of stabilizing products which are necessary in the formats of the prior art (for example $Mg^{2+}$ ions in the kinase activity assays). The method according to the invention, which is precise and adaptable to screening at high flow rates, therefore makes it possible to study the post-translational modifications and test compounds for their ability to modulate these reactions under conditions very close to physiological conditions. In the case where the enzyme is overexpressed, the method according to the invention also makes it possible to study only one given enzyme.

I. THE THREE FORMATS FOR THE DETECTION OF POST-TRANSLATIONAL MODIFICATIONS ACCORDING TO THE INVENTION

I.1 Simple Detection of a Post-Translational Modification

In a first implementation, the invention relates to a method in homogeneous medium making it possible to detect a post-translational modification of a protein substrate, the post-translational modification taking place in the intact living cells. This method is based on the heterologous expression by the cell of a fusion protein comprising said protein substrate and a first coupling domain, via an expression vector previously introduced into the cell.

The method according to the invention advantageously uses a pair of FRET partners in order to measure the protein substrate having undergone a post-translational modification: the labelling of the protein substrate having undergone the post-translational modification by the FRET partner fluorescent compounds is carried out via a coupling domain/coupling agent pair as described below, and by means of a binding domain specifically recognizing the site of the protein substrate having undergone the post-translational modification, according to the diagram on FIG. 10.

When the protein substrate undergoes a post-translational modification, the two fluorescent FRET partner compounds will be situated in proximity to one another and generate a FRET signal.

This method for detection in homogeneous medium of a post-translational modification of a protein substrate catalyzed by a cell enzyme is therefore characterized in that the post-translational modification reaction takes place in intact living cells, in that these cells comprise a heterologous expression vector coding for a fusion protein comprising the protein substrate and a first coupling domain and in that it comprises the following steps:

(i) Incubation of the cells in the presence or in the absence of a compound to be tested capable of modulating the activity of said enzyme, (ii) Addition to the reaction medium of a first fluorescent compound that is a member of a first pair of FRET partners and that is covalently bonded to a coupling agent capable of binding specifically with the first coupling domain present on the protein substrate, (iii) Addition to the reaction medium of a second fluorescent compound that is a member of this first pair of FRET partners, and that is covalently bonded to a binding domain specific to the site of the protein substrate having undergone the post-translational modification and not binding to the non-modified protein substrate, (iv) Measurement of the FRET signal emitted, this signal being representing the quantity of protein substrate having undergone said modification.

When at least one of the fluorescent compounds is not capable of passing through the plasma membrane of the cells, a step of permeabilization or lysis of the cells is implemented before step (ii) and/or (iii).

I.2. Detection of the Protein Substrate Having Undergone a Post-Translational Modification and Detection of the Total Protein Substrate in Two Different Measurement Media The intensity of the signal measured when the preceding method is implemented of course depends on the quantity of protein substrate having undergone the post-translational modification, but also on the total quantity of protein substrate present in the measurement medium. Generally, the signal measured is all the greater when there is protein substrate in the medium. When the signals specific to a post-translational modification obtained in different measurement media are to be compared, it becomes necessary to standardize these signals since, for example, different populations of cells can exhibit different levels of expression of the heterologous DNA coding for the protein substrate. Moreover, when the method according to the invention is used in order to determine the effect of a potential modulating agent of a post-translational modification (for example, in a medicament screening approach), the fact of measuring the total protein substrate makes it possible to verify that the product to be tested does not result in the death of the cell.

A particular implementation of the invention therefore involves measuring, in addition to the protein substrate having undergone the post-translational modification, a signal representing the total quantity of protein substrate. This second signal can be used to standardize that corresponding to the protein substrate having undergone the post-translational modification, for example by calculating the following ratio: signal corresponding to the modified protein substrate/signal corresponding to the total protein substrate.

This implementation is based upon the use of two pairs of FRET partners, one making it possible to measure the signal corresponding to the modified protein substrate and the other making it possible to measure the signal corresponding to the total protein substrate, and upon the expression by the cell of a fusion protein comprising the protein substrate as well as two coupling domains.

In this implementation, a population of cells is distributed in two separate measurement media, for example in different wells of a multiwell plate, so as to be able to measure the signal corresponding to the protein substrate having undergone the post-translational modification, and to be able to measure the signal corresponding to the total quantity of protein substrate.

This implementation of the method for the detection in homogeneous medium of a post-translational modification of a protein substrate catalyzed by a cell enzyme is characterized in that the post-translational modification reaction takes place in intact living cells, in that these cells comprise a heterologous expression vector coding for a fusion protein comprising (1) the protein substrate, (2) a first coupling domain and (3) a second coupling domain, different from the first coupling domain, said second coupling domain not being affected by the post-translational modification, and in that it comprises the following steps:

(i) Incubation of the cells in the presence or in the absence of a compound to be tested capable of modulating the activity of said enzyme;

(ii) Distribution of the cells incubated during step (i) in two different measurement media;

(iii) Addition to the first measurement medium of a first fluorescent compound that is a member of a first pair of FRET partners and that is covalently bonded to a coupling agent capable of binding specifically to said first coupling domain present on the protein substrate;

(iv) Addition to this same first measurement medium of a second fluorescent compound that is a member of this first pair of FRET partners, and that is covalently bonded to a binding domain specific to the site of the protein substrate having undergone the post-translational modification and not binding to the non-modified protein substrate;

(v) Measurement of the FRET signal emitted by the first measurement medium, this signal representing the quantity of protein substrate having undergone said post-translational modification;

(vi) Addition to the second measurement medium of said first fluorescent compound member of said first pair of FRET partners covalently bonded to a coupling agent capable of binding specifically to said first coupling domain present on the protein substrate;

(vii) Addition to said second measurement medium of a third fluorescent compound constituting with the first fluorescent compound a second pair of FRET partners, this third fluorescent compound being covalently bonded to a coupling agent capable of binding specifically to said second coupling domain;

(viii) Measurement of the FRET signal emitted by the second measurement medium, this signal representing the total quantity of protein substrate;

(ix) Standardization of the signal measured in step (v) by the signal measured in step (viii).

When at least one of the fluorescent compounds is not capable of passing through the plasma membrane of the cells, a step of permeabilization of the cells or of lysis of the cells is implemented before step (ii) or before step (iii) and/or (vi).

It is understood that the measurements carried out in one or other measurement medium can be carried out in any order: they can be carried out in parallel on an automated system, or one after the other.

As the FRET measurements are carried out in different measurement media, the two pairs of FRET partners may or may not have the same spectroscopic characteristics. In other words, the second and third fluorescent compounds can be identical but each must be bonded to a different coupling agent.

This assay format illustrated by the diagram on FIG. 11, wherein: E1=1st coupling domain
E2=2nd coupling domain
PTM=Post-translational Modification
1st pair of FRET partners=A/D1
2nd pair of FRET partners=A/D
Polypeptide=protein substrate
can be, for example, implemented with the following reagents:

An antibody recognizing the modified protein substrate as a binding domain specific to the protein substrate having undergone the post-translational modification, coupled with a fluorescent donor compound D1.

An anti-tag 2 antibody, as coupling agent specific to tag 2, this tag corresponding to a coupling domain present on the protein substrate, coupled with a compatible fluorescent acceptor compound A, for the establishment of a FRET, with the donor D1.

An anti-tag 1 antibody as coupling agent specific to tag 1, this tag corresponding to another coupling domain present on the protein substrate, coupled with a fluorescent donor compound D, which may be D1 but which must be compatible with the fluorescent acceptor compound A for the establishment of a FRET.

Starting from the cell lysate, the quantity of protein substrate having undergone a post-translational modification is measured in a first well using the antibody specific to the modified protein substrate coupled with the fluorescent donor compound (D1) as well as using the anti-tag 2 antibody coupled with the fluorescent acceptor compound A compatible with the fluorescent donor compound D1 for the establishment of a FRET.

In a second well, the total quantity of protein substrate is measured using the anti-tag 1 antibody coupled with a fluorescent donor compound D, which may be D1, but which must be compatible with the fluorescent acceptor compound A for the establishment of a FRET, as well as using the anti-tag 2 antibody coupled with the fluorescent acceptor compound A.

I.3. Detection of the Protein Substrate Having Undergone a Post-Translational Modification and Detection of the Total Protein Substrate in a Single Measurement Medium (FRET Killer)

In a particularly advantageous alternative implementation, the protein substrate having undergone the post-translational modification and the total protein substrate are measured in the same measurement medium: this implementation makes it possible to standardize the variations that could be encountered from one measurement medium to the other in a very effective manner.

This implementation is based upon the use of two pairs of FRET partners—one making it possible to measure the signal corresponding to the modified protein substrate and the other making it possible to measure the signal corresponding to the total protein substrate—and, upon the expression by the cell of a fusion protein comprising the protein substrate as well as two coupling domains, as in the preceding implementation. In order to be able to measure in the same well the two signals "modified protein substrate" and "total protein substrate", a FRET signal suppressing agent is used. In practice, a first pair of FRET partners is introduced into the measurement medium (a pair specific to the total protein substrate or to the modified protein substrate, it does not matter which), then the FRET signal suppressing agent is in turn added to the medium, so as to "switch off" the first signal. The second pair of FRET partners is then formed in the measurement medium and the second signal can be measured.

The FRET signal suppressing agents are described below, with reference to FIG. 12.

This implementation of the method for the detection in homogeneous medium of a post-translational modification of a protein substrate catalyzed by a cell enzyme is characterized in that the post-translational modification reaction takes place in intact living cells, in that these cells comprise a heterologous expression vector coding for a fusion protein comprising (1) the protein substrate, (2) a first coupling domain and (3) a second coupling domain different from the first coupling domain, said second coupling domain not being affected by the post-translational modification, and in that it comprises the following steps:

(i) Incubation of the cells in the presence or absence of a compound to be tested capable of modulating the activity of said enzyme, (ii) Addition to the measurement medium of a first fluorescent compound that is a member of a first pair of FRET partners and that is covalently bonded to a coupling agent capable of binding specifically to said first coupling domain present on the protein substrate, (iii) Addition to the measurement medium of a second fluorescent compound that is a member of said first pair of FRET partners, and that is covalently bonded to a binding domain specific to the site of the protein substrate having undergone the post-translational modification and not binding to the non-modified protein substrate, (iv) Measurement of the FRET signal emitted by the first pair of FRET partners, this signal representing the quantity of protein substrate having undergone said post-translational modification, (v) Addition to the measurement medium of an agent suppressing the FRET signal agent measured in step (iv), (vi) Addition to the measurement medium of a third fluorescent compound covalently bonded to a coupling agent capable of binding specifically to said second coupling domain, this third fluorescent compound being compatible with the first fluorescent compound so as to constitute therewith a second pair of FRET partners, and the first and the second pair of FRET partners having the same spectroscopic characteristics, (vii) Measurement of the FRET signal emitted by the second pair of FRET partners, this signal representing the quantity of total protein substrate, (viii) Standardization of the signal measured during step (iv) by that measured during step (vii).

When at least one of the fluorescent compounds or the FRET suppressing agent is not capable of passing through the plasma membrane, a step of permeabilization of the cells or of lysis of the cells is implemented before step (ii), (iii), (v) or (vi).

It is evident that the order of measurement of the signals is not important: steps (iii)-(iv) and (vi)-(vii) can be reversed in order to measure firstly the signal corresponding to the total protein substrate then the signal corresponding to the modified protein substrate, from the moment when the FRET signal suppressing agent specifically suppresses the first signal emitted in the measurement medium.

This format can be implemented, for example, with the following reagents:

Two fluorescent donor compounds D1 and D2 which can be excited by the same stimulus (for example the same light excitation wavelength), An antibody recognizing the modified protein substrate as a binding domain specific to the protein substrate having undergone the post-translational modification, coupled with a fluorescent donor compound D1.

An anti-tag 2 antibody, as coupling agent specific to tag 2, this tag corresponding to a coupling domain present on the protein substrate, coupled with a fluorescent acceptor compound A compatible with the establishment of a FRET with the fluorescent donor compound D1 and the fluorescent donor compound D2, An anti-tag 1 antibody as coupling agent specific to tag 1, this tag corresponding to another coupling domain present on the protein substrate coupled with a fluorescent donor compound D2, An antibody specific to the donor D1, as FRET suppressing agent between the donor D1 and the acceptor A Starting from the cell lysate, the quantity of protein substrate having undergone a post-translational modification is measured using the antibodies recognizing the modified protein substrate coupled with the fluorescent donor compound D1 and the anti-tag 2 antibody coupled with the fluorescent acceptor compound A. After reading, the FRET suppressing agent, specific to D1 and suppressing the FRET between D1 and A, and the anti-tag 1 antibody, coupled with the fluorescent donor compound D2 are added to the same well. This second reading represents the total quantity of protein substrate.

II. THE PAIRS OF FRET PARTNERS

II.1. The FRET

The method according to the invention makes it possible to adapt the FRET technique to the measurement of post-translational modifications in a cell context. The FRET phenomenon has been widely described in the literature and is a concept known to a person skilled in the art. It is a quantum phenomenon which is produced between two fluorescent molecules close to one another (distance comprised between ten and one hundred Angström) and the emission spectrum of one of which (the fluorescent donor compound) partially covers the excitation spectrum of the other (the fluorescent acceptor compound). When the fluorescent donor compound is excited by a photon, it can transmit its energy to the fluorescent acceptor compound which is then in an excited state and emits light.

A pair of FRET partners within the meaning of the invention is therefore constituted by a fluorescent donor compound the emission spectrum of which partially covers the excitation spectrum of the fluorescent acceptor compound. The concept of FRET partners is well known to a person skilled in the art who is capable, on the basis of the spectroscopic characteristics of the known fluorescent compounds, of selecting the pairs of fluorescent compounds compatible in terms of FRET. He may moreover refer to the work by Lakowicz (1999) Principles of fluorescence spectroscopy, $2^{nd}$ edition, Kluwer academic/plenum publishers, NY. Moreover, the term FRET is used here in the broad sense and includes time-resolved FRET (TR-FRET).

The FRET phenomenon can be detected by the measurement of different parameters of the fluorescence signal emitted either by the fluorescent donor compound, or by the fluorescent acceptor compound, or by both compounds. Among the most common techniques, there can in particular be mentioned:

The measurement of the reduction in the donor's fluorescence induced by the FRET phenomenon, The measurement of the increase in the fluorescent acceptor compound's fluorescence induced by the energy originating from the fluorescent donor compound through the FRET, The determination of the ratio (increase in fluorescence of the fluorescent acceptor compound)/(reduction in fluorescence of the fluorescent donor compound), The measurement of the reduction in the fluorescence lifetime of the fluorescent donor compound induced by the FRET phenomenon. The latter is in particular measured by the "Fluorescence Lifetime Imaging Microscopy" technique (FLIM), The measurement of the increase in the fluorescence of the fluorescent donor compound involved in a FRET after the photobleaching of the fluorescent acceptor compound. This technique of photobleaching is known by the name of "Fluorescence Recovery After Photobleaching" (FRAP).

The expression "measurement of the FRET signal" used in the description of the invention designates any one of these techniques equally. The measurement of the fluorescence emitted by the fluorescent acceptor compound is nevertheless one of the preferred approaches for the implementation of the invention.

II.2. The Fluorescent Compounds

The fluorescent compounds can be chosen from the following group: the luminescent proteins such as green fluorescent protein (GFP) or its variants, fluorescent proteins extracted from corals, phycobiliproteins, such as B-phycoerythrin, R-phycoerythrin, C-phycocyanin, the allophycocyanins, in particular those known by the name XL665; the luminescent organic molecules such as the rhodamines, the cyanines, the squaraines, the fluorophores known by the name BODIPY, the fluoresceins, the compounds known by the name ALEXA FLUOR (fluorescent dyes); the supra-molecular complexes such as the rare earth cryptates, the rare earth chelates (in particular europium, terbium, samarium, dysprosium, neodymium chelates and cryptates); luminescent inorganic particles such as nanocrystals ("quantum dots"). These fluorescent compounds can be used either as the fluorescent donor compounds or as the fluorescent acceptor compounds in a FRET system.

The rare earth complexes are known compounds which are described for example in the patents U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761, 481, U.S. Pat. No. 4,801,722, U.S. Pat. No. 4,794,191, U.S. Pat. No. 4,637,988, U.S. Pat. No. 4,670,572, U.S. Pat. No. 4,837,169, U.S. Pat. No. 4,859,777. Other chelates are compounds of a nonadentate ligand such as terpyridine (EP 403 593, U.S. Pat. No. 5,324,825, U.S. Pat. No. 5,202,423, U.S. Pat. No. 5,316,909). The rare earth can be europium or terbium.

The rare earth cryptates are described in particular in the patents EP 0 180 492, EP 0 601 113 and the application WO 01/96 877.

Advantageously, the rare earth complex is a europium chelate or cryptate. When the rare earth is europium, the rare earth complex is preferably a rare earth cryptate with a pyridine unit, still more preferably with a trisbipyridine and pyridine-bipyridine unit.

II.3. Fluorescent Compound/Coupling Agent or Fluorescent Compound/Binding Domain Conjugates In order that a pair of FRET partners can emit a signal in the presence of a protein substrate having undergone a post-translational modification, one of these partners must be conjugated, preferably covalently bonded, to an element recognizing said protein substrate having undergone the post-translational modification. In the case in point, one of the fluorescent compounds, either the fluorescent donor compound or the fluorescent acceptor compound, is covalently bonded to a binding domain (antibody, aptamer etc.) capable of recognizing the site of the protein substrate having undergone the post-translational modification. The other member of the pair of FRET partners is covalently bonded to a coupling agent capable of binding, covalently or non-covalently, to a coupling domain present on the protein substrate (protein tag, suicide enzyme etc.).

The binding domain capable of recognizing the site of the protein substrate having undergone the post-translational modification can be variable in nature: it can be, for example, an antibody, an antibody fragment or an aptamer binding specifically to the site of the protein substrate having undergone the post-translational modification.

The production of antibodies specific to a post-translational modification forms part of the general knowledge of a person skilled in the art and is in particular described in "Antibodies: a laboratory manual" (Ed. Harlow D. Lane, Cold Spring Harbor Laboratory, 1988). It is based on the immunization of a mammal with an antigen comprising the site of the protein substrate as present in the cell after post-translational modification. A useful antibody in the invention can be a complete antibody, or an antibody fragment which can be a Fab or F(ab)'2 or single-chain Fv fragment. The antibody can be recombinant or non-recombinant. In the case of a protein substrate undergoing a group transfer, for example the phosphorylation of an amino acid (serine, threonine or tyrosine), the antigen used for the immunization will comprise a sequence of 5 to 100 amino acids, or 5 to 50 or 5 to 15 amino acids one of which is a phosphorylated serine, or threonine, or tyrosine.

Numerous antibodies specific to post-translational modifications are commercially available. They are, for example, antibodies specific to phospho-serine, phospho-tyrosine, phospho-threonine (Upstate Biologicals, new England Biolabs etc.).

The aptamers which are of polynucleotide nature are single-strand oligonucleotides which have been selected for their ability to bind specifically to a given molecule, in the case in point to a domain of a protein substrate having undergone a post-translational modification. The methods for the preparation and selection are known and in particular described in the patent U.S. Pat. No. 5,567,588 (SELEX method).

The aptamers which are of peptidic nature are constituted by a short sequence of 10 to 20 amino acids ("variable" domain conferring the specificity of the aptamer for a given target), the two ends of which are linked to a "scaffold", protein thus creating a structural constraint participating in the specificity of the peptide aptamer. The methods for the selection and production of these aptamers are also known and described in the prior art.

Depending on the post-translational modifications studied, other binding domains can recognize the sites of the modified protein substrate: in the case where the post-translational modification is a glycosylation, the binding domain can be a lectin such as WGA ("Wheat Germ Agglutinin").

The phosphate groups present on the proteins having undergone a phosphorylation can be recognized by microbeads onto which metallic ions have been grafted. In this case, the binding domain specific to the modified substrate is therefore a microbead (technology known by the name of "IMAP" for "Immobilized Metal Ion Affinity").

In the case of glutathionylation of a protein substrate, GST can be used as a specific binding domain recognizing the glutathion group grafted to the protein substrate.

In the case where the total protein substrate is also to be measured, i.e. in order for a pair of FRET partners to be able to emit a FRET signal in the presence of a protein substrate (whether or not it has undergone a post-translational modification), each of the members of the pair of FRET partners is conjugated, preferably covalently bonded, to a coupling agent (antibody, suicide enzyme substrate etc.) capable of binding, covalently or non-covalently, to a coupling domain present on the protein substrate (protein tag, suicide enzyme etc.). This means, in the case where the total protein substrate is to be measured, that the protein substrate comprises two different coupling domains, one for the fluorescent donor compound and one for the fluorescent acceptor compound.

A person skilled in the art is able to prepare such fluorescent compound/coupling agent or fluorescent compound/binding domain conjugates by the standard conjugation technique using standard reaction groups such as those described, for example, in: "Bioconjugate Techniques", G. T. Hermanson, Academic Press, 1996.

III. FUSION PROTEIN COMPRISING THE PROTEIN SUBSTRATE AND A COUPLING DOMAIN

As mentioned above, the cells on which the method according to the invention is carried out include an expression vector comprising a nucleic sequence coding for a fusion protein constituted by the protein substrate capable of undergoing the post-translational modification that is being studied, and at least one coupling domain which is recognized by the coupling agent bonded to one of the FRET partners.

The choice of the protein substrate depends on the post-translational modification that is to be studied and a person skilled in the art can easily make this choice. By way of information, Table 2 provides a few examples of protein substrates depending on the post-translational modifications studied.

The protein substrate can have the same sequence as the "natural" substrate of the enzyme involved in the reaction that is to be studied: the expression vector can therefore contain a nucleic acid sequence coding for example for a protein receptor, a protein enzyme such as for example a kinase which can undergo a post-translational phosphorylation etc.

The protein substrate can also be constituted by a fragment of the natural substrate, providing that this fragment comprises the domain recognized by the enzyme and the domain undergoing the post-translational modification.

Finally, the protein substrate can be an artificial peptide substrate, such as for example the substrates described in the Application WO03/087400.

In a first implementation, the coupling domain fused with the protein substrate is a protein tag and the coupling agent is an antibody, an antibody fragment or an aptamer specific to said tag. The tag can be any peptide sequence of 4 to 250 amino acids, preferably 4 to 50, and still more preferably 4 to 15 amino acids, providing that this tag does not impede the recognition of the substrate by the enzyme catalyzing the post-translational modification reaction. This tag can be naturally present in the protein substrate capable of undergoing the post-translational modification or be added as described in the experimental part.

In particular, this protein tag is chosen from: glutathione S-transferase, avidin, a peptide constituted by 6 histidines, a peptide constituted by the amino acids 410-419 of the human Myc protein (EQKLISEEDL) (SEQ ID No. 4), a FLAG peptide with the sequence DYKDDDK (SEQ ID No. 3), an influenza hemagglutinin epitope with the sequence YPYDVPDYA (SEQ ID No. 5).

In a second embodiment, the coupling domain fused to the protein substrate is a suicide enzyme and the coupling agent is a substrate of this enzyme.

The suicide enzymes are proteins which have an enzymatic activity modified by specific mutations which confer upon them an ability to bind rapidly and covalently to a substrate. These enzymes are designated suicide enzymes as each one can bind only to one single fluorescent molecule, the activity of the enzyme being blocked by the fixing/binding of the substrate.

At present, two families of known suicide enzymes allow this type of labelling:

The mutant of an alkylguanine-DNA alkyltransferase (or "SNAPTAG" marketed by the company Covalys (WO 02/083937 A2). In the case where this enzyme is used as a coupling domain, the coupling agent bonded to the fluorescent compound is benzyl-guanine or a benzylguanine derivative.

The mutant of a dehalogenase ("HALOTAG" marketed by Promega) which also generates a suicide-type enzymatic reaction (WO 2004/072232 A2). Where this enzyme is used as a coupling domain, the coupling agent bonded to the fluorescent compound is a chloroalkane.

In a third embodiment, the coupling domain is the enzyme Dihydrofolate reductase and the coupling agent is a Dihydrofolate reductase inhibitor, such as the antibiotic Trimethoprim or 5-(3,4,5-trimethoxybenzyl)pyrimidine-2,4-diamine (technology marketed under the name of "LIGANDLINK" by Active Motif).

The expression vector present in the cell, coding for a fusion protein and comprising at least one coupling domain is produced according to the technique known to a person skilled in the art. More precisely, this expression vector can be a plasmid into which there have been inserted, using restriction enzymes and ligases, the nucleic acid sequences coding for the fusion protein which is to be expressed by the cell. These sequences are integrated into the plasmid downstream of a promoter and in the same reading frame. Numerous expression vectors are commercially available.

Similarly, the protocols for the transfection of cells by an expression vector come within the routine techniques described in the literature.

The expression of this fusion protein by the cell can be stable or transitory, according to whether or not the expression vector is integrated into the cell DNA.

IV. PERMEABILIZATION OF THE CELL MEMBRANE/USE OF FLUORESCENT COMPOUNDS CAPABLE OF PASSING THROUGH THE CELL MEMBRANE

The method according to the invention has the advantage of allowing the detection of a post-translational modification taking place in a living cell, under conditions very close to physiological conditions. Nevertheless, once the post-translational modification reaction has taken place, it may be necessary to permeabilize the cell membrane prior to the addition of the FRET partner compounds in order to allow them to reach their target in the cell. The permeabilization of the cell membrane can be carried out by any appropriate method (Goncalves et al. (2000) Neurochem. Res. 25: 885-8). These methods include the addition of a detergent (for example: CHAPS, cholic acid, deoxycholic acid, digitonin, n-dodecyl-, 8-D-maltoside, lauryl sulphate, glycodeoxycholic acid, n-lauroylsarcosine, saponin or TRITON X-100® (octylphenol ethyelene oxide condensate)) or of an organic alcohol (such as methanol or ethanol) to the culture medium. Other permeabilization techniques involve the use of peptides or toxins (Aguilera et al. (1999) FEBS Lett. 462: 273-277; Bussing et al. (1999) Cytometry 37: 133-139).

A person skilled in the art is able to choose the permeabilizing agent and adapt the experimental conditions (in particular its concentration and duration of incubation) in order to permeabilize the cells satisfactorily, i.e. in such a manner that the pairs of FRET partners can penetrate into the cell.

Within the meaning of the invention, permeabilization includes the lysis of the cells: once the post-translational modification has taken place in a cell context, it is no longer necessary to maintain the integrity of these cells. The addition of the FRET partners allowing the detection of the protein substrate having undergone the modification and/or optionally those allowing the detection of the total protein substrate, can be carried out on a cell lysate and not necessarily on a population of intact living cells.

Alternatively, it is also possible within the scope of the invention to use fluorescent conjugates which are capable of passing through the plasma membrane, either because they are "naturally" capable of this because of their chemical structure, or because they comprise a domain allowing them to pass through the cell membrane.

The following techniques can be used in order to make the fluorescent compounds capable of passing through the plasma membrane:

1) Use of esters which mask the charged groups during the passage through the lipid bilayer. These esters come within the category of the compounds named "pro-drugs" and refer to compounds which are rapidly transformed in vivo in order to produce the "parent" compound following hydrolysis under physiological conditions (T. Higuchi and V. Stella (1975) in "Pro-drugs as Novel Delivery Systems", Vol. 14 of the A.C.S. Symposium Series, American Chemical Society). Examples include mainly the pivaloyl-oxymethyl, acetoxymethyl groups as well as the glycol esters (Nielsen and Bundgaard (1984) Int. J. of Pharmacy 39: 75-85). When this technique is used, one of these esters is grafted covalently onto the fluorescent compound.

2) Use of viral peptides grafted covalently onto the fluorescent compound. Certain viral peptides make it possible to convey the fluorescent compound through the cell membrane. As examples of such viral peptides, there can be mentioned the analogues of "penetratin" and "transportan" (Langel et al. (2000) Bioconj. Chem. 11: 619-626), the poly-Arginines (Wender et al. (2003) Org. Lett. 5(19): 3459-3462), the peptoids (analogues of peptides carrying guanidine groups (Wender et al. (2000) Proc. Natl. Acad. Sci. USA, 13003-8)), or the non-hydrolyzable derivatives with tetraguanidinium units (Fernandez-Carneado et al. (2005) J. Am. Chem. Soc. 127: 869-874).

3) Modification of the lipophily and polarity of the fluorescent compounds by adding side chains containing cholesterol molecules, vitamin E or aliphatic chains which interact with the cell membranes by using the illustrated approach on oligonucleotides using undecyl- or 1,2-di-O-hexadecyl-glycerol chains (Rait et al. (2000) Bioconj. Chem. 11: 153-160). These modifications are more effective than the cationic surfactants (cationic "lipids") which form supramolecular complexes with the nucleic acids and increase endocytosis but which are toxic and damage the cell membranes.

As a result, in the process according to the invention, at least one fluorescent compound comprises a domain allowing it to pass through the plasma membrane, this unit being selected from the following groups: esters such as pivaloyl-oxymethyl ester, acetoxymethyl ester, or glycol esters; viral peptides carried by membrane transporters such as penetratin and its analogues, transportan and its analogues, the polyarginine groups, the peptoids carrying guanidine groups, such as the oligoguanidinium groups; cholesterol groups, vitamin E or aliphatic chains such as undecyl or 1,2-di-O-hexadecyl-glycerol chains.

V. FRET SUPPRESSING AGENTS

A particularly advantageous implementation of the invention involves measuring the signal corresponding to the protein substrate having undergone a post-translational modification and the signal corresponding to the total protein substrate in the same measurement medium. For this purpose, a FRET suppressing agent is used as described above.

By FRET signal suppressing agent is meant a compound which causes a FRET signal reduction of at least 70% relative to the signal measured in the absence of this compound. The FRET signal suppressing agents causing a FRET reduction of at least 80%, or of at least 90%, are preferred.

The FRET signal suppressing agents used in the method according to the invention do not disturb the biological event studied (post-translational modification) to the extent that they act at the level of one of the fluorescent compounds involved in the FRET, and not at the level of the biological event studied. They have no effect on the distance separating the molecules involved in the biological event.

In order to determine whether a compound is a FRET signal suppressor within the meaning of the invention, it can be placed in contact with a pair of FRET partner fluorescent conjugates emitting a FRET signal, for example two fluorescent conjugates recognizing the same molecule, or two fluorescent conjugates one of which comprises a biotin and the other streptavidin. The FRET signal emitted by the reaction medium is measured in the presence and in the absence of said compound, the FRET signal suppressors being those which lead to a reduction in signal of at least 70%. This simple test allows a person skilled in the art to isolate FRET suppressing agents within the meaning of the invention.

These FRET suppressing agents can be different in nature and have different functions, but they make it possible, in all cases, to suppress the FRET signal emitted by a given donor-acceptor pair. The FRET suppressing agents can be of four types.

a) FRET Signal Suppressing Agents Acting by Specific Fixing/Binding by Non-Covalent Binding to One of the Fluorescent Compounds Involved in the FRET:

These agents have a domain allowing specific and non-covalent binding with the fluorescent compound. They can be chosen from: proteins, in particular antibodies or fragments of antibodies, peptides or aptamers, each having a binding domain for one of the FRET partner fluorescent compounds.

A person skilled in the art has techniques making it possible for him to produce these compounds and to test their binding to fluorescent compounds. These are, for example, the standard techniques of antibody production, or the "SELEX" method for the selection of aptamers.

Preferred FRET signal suppressing agents are, in the case of a FRET involving a rare earth chelate or cryptate, the compounds capable of binding non-covalently to rare earth cryptates or chelates, such as for example: proteins, in particular antibodies or fragments of antibodies, peptides, or aptamers possessing a binding domain for a rare earth cryptate or chelate.

Still more preferred FRET signal suppressing agents are the anti-rare earth chelate or anti-rare earth cryptate antibodies.

The anti-cryptate antibodies are produced by the technique well known to a person skilled in the art, by immunizing a mammal with an antigen.

In the case where the antigen is small in size, as is the case with rare earth cryptate, it must be coupled with an immunogen-carrying molecule. For this purpose, the cryptate is functionalized, as described in the patent EP 321 353. Preferably, an alkylamine arm is grafted onto the cryptate.

The carrier molecules can be chosen from: bovine serum albumin (BSA) or cationic BSA (cBSA), KLH (Keyhole Limpet Hemocyanine), thyroglobulin, ovalbumin. The carrier molecules can also be liposomes or synthetic carrier molecules such as L-lysine polymers, or L-glutamic acid, ficoll, dextran, or polyethylene glycol. These carrier molecules generally comprise functional groups which react with the functionalized cryptate, or such groups can be introduced by standard techniques. Preferably, a rare earth cryptate carrying an alkylamine group is conjugated with the BSA.

The immunogen thus obtained is then mixed with an adjuvant, such as for example Freund's adjuvant, in order to form a solution.

Mammals—for example mice—are immunized by subcutaneous injection of this solution, and after a period necessary for the induction of immunity, the sera of the animals are collected and the polyclonal antibodies purified, for example by affinity chromatography.

The anti-cryptate monoclonal antibodies are produced using various techniques known to a person skilled in the art. By way of example there can be mentioned the techniques originating from the works of Köhler and Milstein: a few weeks after the immunization, the spleen of the mouse immunized with the antigen is removed. A mixture of lymphocytes and plasmocytes originating from this spleen is fused in vitro with myelomatous cells in the presence of a cell fusion inducer, such as polyethylene glycol. A mutant myelomatous cell line, devoid of hypoxanthine guanosine phosphoribosyl transferase (HGPRT), is used in order to make it possible to easily select the hybrid cells. These cells are cultured in a medium containing hypoxanthine, aminopterine (methotrexate) and thymine (HAT medium) in order to eliminate the non-fused myelomatous cells and to select the hybridomas of interest. The non-fused spleen cells die as they are not capable of proliferating in vitro. The hybrid cells, on the other hand, survive. The hybridomas thus obtained are cultured in the well of a cell culture plate. The supernatants of these wells are tested for the presence of specific anti-rare earth cryptate antibodies in a simple screening test such as ELISA or RIA. The hybridomas are then cloned and can be injected into mammals in order to induce myelomes secreting a large quantity of anti-cryptate antibodies in the ascitic liquid.

The polyclonal or monoclonal anti-rare earth cryptate antibodies obtained can then be tested for their ability to suppress the FRET signal emitted by a pair of FRET partners comprising said rare earth cryptate as fluorescent energy donor compound. For this purpose, the procedure as described above and in Example 1 presented below can be followed.

b) FRET Suppressing Agents Acting by Decoupling of the Fluorescent Compound with the Biological Event:

As described above, the study of biological events using the FRET phenomenon is based on the labelling of molecules involved in the biological event by FRET partner fluorescent compounds. If this labelling is carried out in non-covalent manner, via binding partners, it is possible to uncouple one of the fluorescent compounds from the biological event.

For example, if a molecule involved in the biological event is covalently bonded to a member of a pair of binding partners (for example a single-strand oligonucleotide), and that fluorescent compound is covalently bonded to the other member of this pair (for example a complementary single-strand oligonucleotide), then the addition to the measurement medium of the first member of this pair (the first single-strand oligonucleotide, in free form) will uncouple the labelling of the biological molecule by the fluorescent compound, by a competition phenomenon according to the diagram on FIG. 13:

These FRET signal suppressing agents are therefore members of pairs of binding partners, and can of course only be used as FRET signal suppressing agents if their partner is grafted onto the molecule involved in the biological event studied. They can be chosen from the members of the following pairs: complementary single-strand nucleic acids, tag/anti-tag and in particular the members of the pairs: DNP/anti-DNP antibodies, in which DNP represents dinitrophenol; GST/anti-GST antibodies in which GST represents glutathione S-transferase; biotin/avidin; 6HIS/anti-6HIS antibodies in which 6HIS is a peptide constituted by 6 histidines; Myc/anti-Myc antibodies in which Myc is a peptide constituted by the amino acids 410-419 of the human Myc protein; FLAG®/anti-FLAG® antibodies in which FLAG® is a peptide having the following 8 amino acids: DYKDDDDK (SEQ ID No. 3), HN anti-HA antibodies in which HA is an Influenza hemagglutinin epitope.

c) FRET Suppressing Agents Acting by Modification of the Nature of the Fluorescent Compound:

Where the fluorescent compound is a rare earth chelate, the FRET suppressing agents can reduce the stability of the fluorescent compound by entering into competition either with the rare earth for binding to the chelate, or with the chelate for binding to the rare earth.

For example, the addition to the measurement medium of an ion which will enter into competition with the rare earth for binding to the chelate can encourage the formation of a new non-fluorescent chelate/ion complex. Such an ion can be the Manganese $Mn^{2+}$ ion in the case of the rare earth chelates.

As an example of competition with the chelate, there can be mentioned the use of agents complexing metals such as EDTA which will result in the formation of a non-fluorescent EDTA-rare earth complex, to the detriment of the fluorescent chelate-rare earth complex.

Moreover, certain fluorescent compounds are sensitive to the variations in ionic strength of the medium: this is the case in particular with the fluorescent protein compounds comprising several sub-units linked by electrostatic bonds, and the quaternary structure of which is destabilized during a reduction in the ionic strength of the medium. There can be mentioned by way of example the case of allophycocyanin, which dissociates under these conditions. When such fluorescent compounds are used, the FRET signal can therefore be suppressed by reducing the ionic strength of the reaction medium.

d) FRET Suppressing Agents Acting by Modification of the Photophysical Properties of the Fluorescent Compound:

This type of FRET suppressing agents results in a fluorescence extinction effect (also called "quenching").

There can be mentioned by way of example uric acid which, where the fluorescent compound is a rare earth chelate or cryptate, can cause oxidation-reduction reactions of the rare earth which can lead to a suppression of the FRET.

Other fluorescent compounds are sensitive to variations in pH and the agents modifying the pH can in this case also be used as FRET signal suppressing agents.

In general, the agents modifying a fluorescent compound emission or absorption spectrum, or those inhibiting fluorescence can be used in the methods according to the invention, providing that they effectively cause a suppression of the FRET signal within the meaning of the invention. This characteristic can be tested simply as mentioned above.

VI. ENZYME CATALYZING THE POST-TRANSLATIONAL MODIFICATION AND OTHER PROTEINS INVOLVED IN THE POST-TRANSLATIONAL MODIFICATION

In a particular implementation of the invention, the enzyme catalyzing the post-translational modification is expressed by an expression vector integrated by the cell in a stable or transitory manner. The sequences of these enzymes are available in the literature and their expression comes within the routine techniques for a person skilled in the art. This implementation makes it possible to overexpress the enzyme involved and therefore to amplify the signal measured since a larger quantity of protein substrate is potentially modified. Moreover, the overexpression of the enzyme increases the specificity of the signal with respect to the other cell enzymes and therefore allows the study of a given enzyme. This implementation also makes it possible to control the expression of the enzyme if the expression vector comprises a regulation domain such as an inducible promoter or an "enhancer" sequence. The use of a system allowing the expression of inducible enzymes makes it possible to detect the allosteric inhibitors which act directly on the enzyme by stabilizing the latter in its inactive form. It is important to note that, even in the case where the enzyme is overexpressed, the post-translational modification reaction always takes place in an environment close to physiological conditions, in particular in the case of the reactions involving a group transfer since the group donor is present in the cell at physiological concentrations.

Certain enzymes catalyzing a post-translational modification are not constitutively active and must be activated. The methods according to the invention can therefore comprise an additional step of activation of the enzyme involved in the reaction studied.

This stimulation can be: an osmotic shock, thermal shock, oxidative stress induced by a chemical compound (for example by the addition of $H_2O_2$ or diamine to the culture medium). Carcinogenic compounds, heavy metals (for example mercury, cadmium etc.) or pollutants can also be used as chemical activators.

This stimulation can also be biochemical in nature by the addition, to the culture medium, of growth factors (such as the EGFs, the FGFs, the CSFs, the HGFs, IGFs, ILGFs, NGFs, PDGFs, VEGFs), cytokines (such as the interleukins IL-1, IL-2, IL-6, IL-8), the interferons IFN-α and IFN-β, TNFα, TNFβ, growth hormones (such as PL, GH, Prl) or neuromediators (such as acetylcholine, glycine, glutamate, GABA, dopamine, noradrenaline, histamine).

A person skilled in the art is able to assess in which cases these post-translational modification stimulating agents must be used, depending on the enzyme involved.

In an alternative implementation, the method according to the invention is implemented using cells expressing a protein involved in the activation cascade leading to the post-translational modification. These proteins can, for example, be a transmembrane receptor, such as a receptor coupled to G protein, or an enzyme producing an intracellular messenger (such as adenylate cyclase) the activation of which results, via an intracellular signalling cascade, in the modification of the protein substrate capable of undergoing the post-translational modification.

According to this implementation, the cells contain an expression vector integrated into the cell in a stable or transitory manner, and coding for a protein involved in the activation route leading to the post-translational modification. Depending on the post-translational modification studied, a person skilled in the art is able to choose the protein in question. This implementation is particularly useful, for example, for studying the effect of candidate compounds capable of acting on said protein involved in the activation route of the post-translational modification.

VII. CELLS CO-EXPRESSING A PROTEIN SUBSTRATE COMPRISING AT LEAST ONE COUPLING DOMAIN AND THE ENZYME CATALYZING A POST-TRANSLATIONAL MODIFICATION OR A PROTEIN INVOLVED IN THE POST-TRANSLATIONAL MODIFICATION

The invention also relates to cells suited to the implementation of the methods according to the invention.

These cells suited to the study of a post-translational modification are characterized in that they comprise:
a) an expression vector coding for a fusion protein comprising the protein substrate and one or two coupling domains; and
b) an expression vector comprising the nucleic acid sequence coding for the enzyme catalyzing said post-translational modification or for a protein involved in the activation cascade leading to the post-translational modification.

The protein involved in the activation cascade leading to the post-translational modification is, preferably, a membrane receptor or an enzyme producing an intracellular massager.

As mentioned above, these expression vectors can for example be plasmids. The cells can in particular be cells of mammals, in particular human cells.

In a particular implementation, the expression vectors are integrated into the cellular DNA. In a preferred implementation the expression vectors are integrated into the cellular DNA and the cells are immortalized cells, which makes it possible to obtain stable cell lines, which are particularly advantageous for studying a post-translational modification under easily reproducible conditions.

Although the cells according to the invention have never been described, the co-transfection of expression vectors into a cell and the obtaining of immortal cell lines expressing "exogenous" proteins in a stable manner (in the case in point the protein substrate comprising at least one binding domain and the enzyme catalyzing the post-translational modification studied or a protein involved in the activation cascade leading to the post-translational modification) are techniques known to a person skilled in the art.

VIII. POST-TRANSLATIONAL MODIFICATIONS WHICH CAN BE DETECTED BY MEANS OF THE INVENTION

The method according to the invention cannot be limited to a given post-translational modification. In fact, the work carried out by the Applicant can be easily transposed to the majority of post-translational modifications involving a group transfer onto a protein substrate, a cleavage of a group present on a protein substrate, or a protein substrate cleavage.

The method according to the invention is particularly suited to the study of the following post-translational modifications:

mono ADP ribosylation: transfer of an ADP-ribose to an Arginine or Cysteine residue of the protein to be modified, a reaction catalyzed by a mono ADP-ribosyl transferase.

The mono ADP ribosylation plays a fundamental role in the cell signalling, as well as in the modification of the cytoskeleton by targeting the actin as well as the desmin filaments.

poly ADP ribosylation: transfer of polyADP-ribose to a glutamic acid residue of the protein to be modified, a reaction catalyzed by a poly ADP-ribose polymerase.

The poly-ADP ribosylation of nuclear proteins by the Poly ADP ribose polymerases (PARP) constitutes one of the cell's responses to DNA lesion.

Phosphorylation: transfer, by a Kinase, of the γ phosphate of ATP to a hydroxyl group of a Serine, Threonine, Tyrosine or Histidine of the protein to be modified. The phosphorylation of proteins is a central element in the transduction of the signal within the cell. The kinase proteins represent a large family of enzymes sharing a common structure. These enzymes control a large number of intracellular mechanisms which include the transcription and translation of genes, the regulation of the cell cycle, the growth and differentiation of cells, the cell metabolism as well as apoptosis. The deregulation of the kinasic activities is frequently involved in cell dysfunctions. The main protein kinase families are listed in Table 1.

TABLE 1

Main Kinase Families

| Type of kinase | Sub-family |
|---|---|
| Tyrosine kinase activity receptors | ALK ("anaplastic lymphoma kinase"), AXL or ARK ("adhesion-related kinase"), DDR ("discoidin domain receptor"), EGFR ("epidermal growth factor receptor"), EPH ("ephrin receptor"), FGFR ("fibroblast growth factor receptor"), INSR ("insulin receptor kinase"), MET, MUSK ("muscle specific kinase"), PDGFR ("platelet-derived growth factor receptor", in particular the receptors: PDGFRα, PDGFRp, CSFIR, c-Kit, c-fms) PTK7 ("protein tyrosine kinase 7"), RET, ROR ("receptor tyrosine kinase-like orphan receptor"), ROS, RYK ("atypical orphan receptor tyrosine kinase"), TIE, TRK ("tropomyosin-related kinase"), VEGFR ("vascular endothelial growth factor receptor", in particular the receptors VEGFR1, VEGFR2, VEGFR3") AATYK ("apoptosis-associated tyrosine kinase") |
| Intra-cellular/ cytosoluble Tyrosine Kinases | ABL ("Abelson tyrosine kinase"), ACK ("acetate kinase"), CSK ("C-terminal Src kinase"), FAK ("focal adhesion kinase"), FES, FRK ("fyn-related kinase"), JAK ("Janus kinase", in particular the proteins Jak1, Jak2, Tyk2 and Jak3) SCR (in particular the proteins Src, Yes, Fyn, Lyn, Lck, Blk. Hck, Pgr and Yrk) TEC, SYK ("spleen tyrosine kinase", in particular the proteins Syk and ZAP70) |
| Serine/Threonine Kinases of AGC type ("cyclic nucleotide dependent kinase") | AKT or PKB ("protein kinase B"), PKA ("cAMP-dependent kinase"), SGK ("serum/glucocorticoid regulated kinase"), PKC ("protein kinase C"), PDPK/PDK ("phosphoinositide-dependent protein kinase"), DMPK ("dystrophia myotonic-protein kinase) S6K (ribosomal protein S6 kinase") |
| CMGC | CDK ("cyclin dependent protein kinase, in particular CDK1, CDK2, CDK4 and CDK6") MAPK/ERK ("nitrogen-activated protein kinase/extracellular signal regulated kinase"), GSK3 ("glycogen-synthase kinase 3") |

TABLE 1-continued

Main Kinase Families

| Type of kinase | Sub-family |
|---|---|
| Serine/Threonine Kinase of CAMK type ("calcium/Calmodulin dependent protein kinase") | CaMK I/IV, CaMK II, MAGUK (or CASK for "calcium/calmodulin-dependent serine protein kinase"), DCaMKL ("double cortin and calcium/calmodulin-dependent protein kinase"). |
| Casein Kinases | CK1 and CK2 |
| Tyrosine kinase like | IRAK ("Interleukin-1 receptor associated kinase") 1 to 4 RIPK ("Receptor interacting protein kinase") 1 to 3 LRRK ("Leucine rich repeat kinase") 1 and 2 LIMK ("Lim domain-containing kinase") 1 and 2 TESK ("Testis specific kinase") 1 and 2 MLK ("Mixed lineage kinase") 1 to 4 ZAK KSR ("kinase suppressor of RAF") RAF (1, A, B) BMPR ("Bone morphogenic protein receptor") ActR ("Activin receptor") |
| Sterile | COT ("Cancer osaka thyroid") kinase MAP3K ("Mitogen activated protein kinase kinase kinase") 1 to 8 MAP2K ("Mitogen activated protein kinase kinase") 1 to 7 MST ("Mammalina sterile") 1 to 4 PAK ("p21 activated kinase") 1 to 3 LOK ("Lymphocyte oriented kinase") SLK ("Sterile 20 like kinase") |

Acetylation: transfer of an acetyl group, by acetyltransferases, from the acetyl-CoA to the ϵ-NH2 functions of the lysine residues of the protein to be modified. Acetylation is a post-translational modification which mainly targets the histones. The degree of acetylation of the histones is strongly correlated with the transcriptional activity of the cell. Contributing to the increase in the transcriptional activity, numerous transcription factors are also acetylated. The tumor suppression protein p53 is also acetylated by p300/CBP.

Glutathionylation: transfer of a glutathione group to a Cysteine residue of the protein to be modified as a result of cell stress. This reaction is not catalyzed by a particular enzyme. It is therefore regulated in the cell by the intracellular concentration of the reagents involved.

N-Glycosylation: the oligosaccharyl transferases transfer, from the dolichol pyrophosphate, an oligosaccharide of 14 sugars $Glc_3Man_9GlcNAc_2$ (Glc: Glucose, Man: Mannose, GlcNAc: N acetyl glucosamine) to an asparagine residue (Asn) included in the sequence Asn-X-Ser or Asn-X-Thr (X being able to be any amino acid with the exception of proline) of the protein to be modified. The N-glycosylation takes place in the endoplasmic reticulum and the Golgi apparatus and targets the proteins intended to be secreted or expressed at the cell surface.

O-Glycosylation: transfer of the GlcNAc group from UDP-GlcNAc (Uridine di-phosphate-N-acetyl glucosamine) to the Serine and Threonine residues of the protein to be modified. The O-glycosylations target numerous nuclear and mitochondrial cytoplasmic proteins.

Methylation: transfer of a methyl group from the S-adenosyl-methionine to an arginine residue of the protein to be modified. Eight protein arginine methyl transferases (PRMT 1-8) exist in a mammal capable of this reaction. The methylated proteins often contain repetitions of the RGG or GRG unit. The methylation of the proteins plays multiple roles in the cell mechanisms.

Proteolysis: the peptidases are capable of splitting the proteins using a water molecule to cut the peptide bond. The endopeptidases recognize a primary sequence, a secondary or tertiary structure within the substrate and cut the protein after a determined amino acid. The exopeptidases digest a polypeptide chain from the N or C terminal end. The proteolysis phenomena modulate the activity, the role, the location and the fate of numerous proteins. Proteolysis can lead to the generation of active biomolecules starting from the zymogen, to the destruction of a bioactive protein, or constitute a prerequisite for other post-translational modifications.

Prenylation: covalent addition of a lipid group of farnesyl (15 carbons) or geranylgeranyl type (20 carbons) by creation of a disulphide bridge with a cysteine situated close to the C-terminal end of the protein to be modified. Prenylation allows the membrane anchoring of the protein but also plays a role in the protein-protein interactions. There are three prenyltransferases in humans. Farnesyltransferase and geranylgeranyltransferase 1 recognize the same unit comprising a cysteine ($CA_1A_2X$ box) (SEQ ID No. 37) and catalyze the transfer of a lipid group to this cysteine. If X is a Serine, Methionine, Alanine or Glutamine, then the protein is prenylated by farnesyltransferase; if X is a Leucine then this enzyme is geranylgeranyltransferase 1. Geranylgeranyltransferase 2 transfers the geranylgeranyl group to cysteines situated at the C-terminal end of the protein, said cysteine being comprised in one of the following sequences: XXXCC (SEQ ID No. 38), -XXCXC (SEQ ID No. 39), -XXCCX (SEQ ID No. 40), -XCCXX (SEQ ID No. 41), or -CCXXX (SEQ ID No. 42).

Ubiquitination: attachment of an ubiquitin (protein with 76 amino acids) in covalent manner by an isopeptide bond joining the ϵ-amino group of a lysine residue of the target protein to the C-terminal glycine of the ubiquitin. This process requires the action of three enzymes: a ubiquitin activation enzyme (E1), a ubiquitin transport enzyme (E2) and a ubiquitin ligase (E3). Very numerous forms of these enzymes E1, E2 and E3 exist. A protein can be mono-ubiquitinated on different lysines, or the cycle can be repeated several times, the fixed/bound ubiquitin being ubiquitinated in its turn, leading to an extension of the chain, called poly-ubiquitination (3 to 5 ubiquitins). Depending on the type of polyubiquitin chain formed, either the protein is directed to the proteasome S26 where it is degraded, or it affects the tolerance to DNA lesions, the inflammatory response, the circulation and synthesis of proteins. For its part monoubiquitination plays a role in protein circulation.

Sumoylation: attachment of a SUMO protein "Small Ubiquitin-related Modifier" (polypeptide with 101 amino acids) by isopeptide bond between a lysine residue of the protein to be modified and the C-terminal glycine of the SUMO protein. To date 4 SUMO homologues (SUMO1, SUMO2, SUMO 3 and SUMO 4) have been described. The enzymatic process of Sumoylation is similar to that of ubiquitination, it involves an activation enzyme (E1) (heterodimer Aos1/Uba2), a transport enzyme (E2) (Ubc9) and a ligation enzyme (E3).

Sumoylation plays an important role in the nuclear location of proteins, their DNA repair activity, their transcriptional activity. Sumoylation can also play an antagonistic role as regards ubiquitination.

Nitration: covalent bond between an $NO_2$ and a tyrosine or cysteine of the protein to be modified. This post-translational modification is not catalyzed by an enzyme and therefore depends on the concentration of the reagents involved in the cell. The nitration of the proteins modifies their function and their degradation.

In all cases, the method of study of post-translational modifications according to the invention is implemented on cells expressing a protein substrate capable of undergoing the post-translational modification studied, this protein substrate comprising at least one coupling domain allowing its detection by a FRET technique.

Table 2 illustrates a certain number of post-translational modifications which can be studied using the method according to the invention: in the case of the modifications involving a group transfer catalyzed by an enzyme expressed by the cell (column 2) from a donor group (column 3) to an amino acid (column 4) present on the protein substrate expressed in a stable or transitory manner by the cell (column 5), one of the fluorescent compound members of a pair of FRET partners is covalently bonded to a binding domain specific to the post-translational modification (column 6). The coupling of the fluorescent compound with the specific binding domain is carried out by the standard conjugation technique based on the use of rectional groups, well known to a person skilled in the art and described in "Bioconjugate Techniques", G. T. Hermanson, Academic Press, 1996.

TABLE 2

| Post-translational modification | Enzymes involved | Donor group (case of a modification involving a group transfer) | Amino acid undergoing the modification | Example of protein substrate NP = Genbank ref. Amino acid undergoing the modification in bold type | Binding domain specific to the Post-translational modification |
|---|---|---|---|---|---|
| Mono ADP ribosylation | Mono ADP-ribosyl transferases | β Nicotinamide adenine dinucleotide (βNAD+) | Arginine, Cysteine | CSIYNLKSREGNVKVSREL (SEQ ID No. 6) domain (NP-002066) of the Guanine nucleotide binding protein β3 FDRVTDVIIKNNLKECGLY (SEQ ID No. 7) domain of the protein Gαi3 KYDPTIEDSYRKQVEVDA (SEQ ID No. 8) domain (NP-056461) of Ras Related protein (RAP1B) | Antibodies (Meyer T. et al., Eur. J. Biochem. 1986, 155: 157-165) (Schwab CJ et al. Proc. Soc. Exp. Biol. Med. 2000, 223: 389-396) |
| Poly ADP ribosylation | Poly ADP-ribose polymerases. | β Nicotinamide adenine dinucleotide (βNAD+) | Glutamic acid | | Antibodies (Malik N. et al., Proc. Natl. Acad. Sci USA 1983, 80: 2554-2558) |
| Acetylation | Acetyl-transferases | Acetyl-CoA | Lysine | EWYKKMLDKAVSERIV domain of p53 (SEQ ID No. 9) SAE GAAKEEP (SEQ ID No. 10) domain (NP-004956) of HMG14 | Antibodies |
| Glutathionylation | no enzyme involved | Oxidized Glutathion GSSG | Cysteine | | Glutathione S-transferase (Cheng G. et al. Arch. Biochem. Biophys. 2005, 435: 42-49) Antibodies Messina JP et al. Anticarcinogenesis and Radiation Protection (Eds Cerutti, PA, Nygaard OF, Simic MG) 1987 Plenum Publishing Corp. 407-412. |
| O-Glycosylation | O-GlcNAc Transferase | UDP-GlcNAc (Uridine di-phosphate-N-acetyl glucosamine) | Serine, Threonine | PDYYDY QEVTPRPSEE (SEQ ID No. 11) domain (NP-059453) of Microfibrillar associated protein 2 KFELLPTPPLSPSRRSGLC (SEQ ID No. 12) domain (NP-002458) of c-myc | Antibodies (Snow CM et al. J. Cell. Biol. 1987 104: 1143-1156) |
| N-Glycosylation | Oligosaccharyl transferase | Dolichol-pyrophosphate-GlcNAc2Man9 Glc3 | Asparagine | IESPVVQLHSNFTAVCVL (SEQ ID No. 13) domain (NP-002175) of the b chain of the IL6 receptor VCPGMDIRNNLTRLHELE (SEQ ID No. 14) domain (NP-000199) of the insulin receptor | Lectine (Fan X et al. Anal Biochem. 2004, 332: 178-186) (Opat AS et al. Biochem. J. 2001 358: 33-40) |

TABLE 2-continued

| Post-translational modification | Enzymes involved | Donor group (case of a modification involving a group transfer) | Amino acid undergoing the modification | Example of protein substrate NP = Genbank ref. Amino acid undergoing the modification in bold type | Binding domain specific to the Post-translational modification |
| --- | --- | --- | --- | --- | --- |
| Methylation | Arginine Methyltransferase | S-adenosyl-methionine | Arginine | RGRALPGGRLGGRGRGR (SEQ ID No. 15) domain (NP-001997) of the Fibroblast Growth factor AILKAQVAARGRGRMG (SEQ ID No. 16) (NP-004166) domain of the Small nuclear ribonucleoprotein polypeptide D3 | Antibodies (Côte et al. Mol. Biol. Cell 2002 14: 274-287. Boisvert FM et al. J. Cell. Biol. 2002 23: 957-969) |
| Nitration | no enzyme involved | NO2 | Tyrosine/Cysteine | | Antibodies (S-nitrosylation Gow AJ et al. J; Biol. Chem. 2002 277 9637-9640.) Antibodies (Nitrotyrosine Helman M et al. Biochem. J. 1971 152: 971-974) |
| Phosphorylation | Kinase: see for example Table 1 above | ATP | Serine/Threonine/Tyrosine | S/T-PX-K/R (SEQ ID No. 17) domain recognized by the Cyclin dependent kinase SEFDTGSIIIFF (SEQ ID No. 18) domain recognized by the Casein Kinase I EDEESEDEE (SEQ ID No. 19) domain recognized by the Casein Kinase II KRQQSFDLF (SEQ ID No. 20) domain recognized by the CamK II VTPRTPPPS (SEQ ID No. 21) domain of Erk 1/2 GRPRTSSFAEG (SEQ ID No. 22 ) domain of Akt RRXS/T (SEQ ID No. 23) domain of PKA AXVIYAAPF (SEQ ID No. 24) c-Abl domain EEEEYFELV (SEQ ID No. 25) domain of EGFR XEXIYGVLF (SEQ ID No. 26) domain of Lck | Antibodies, Metal affinity reagent (microbeads, IMAP technology) |
| prenylation | Prenyltransferases | Farnesyl, Geranyl | Cysteine | PQLSDQQVPPHQDCAC (SEQ ID No. 27) domain (NP-002857) of RAB3 YEDDEHHPRG GVQCQTS (SEQ ID No. 28) domain (NP-001530) of Heat shock 40kDa protein | Antibodies (Lin HP et al. J. Gen. Virol. 1999, 80: 91-96) |
| Sumoylation | E1, E2, E3 | SUMO-1, SUMO-2, SUMO-3, SUMO-4 (Gill C et al. Genes and Development 2004, 18: 2046-2059 | Lysine | CFEAHQWFLKHEARPLAE (SEQ ID No. 29) domain (NP-150241) of PML KKEKENGSSPPQIKDEP (SEQ ID No. 30) domain (NP-003277) of DNA topoisomerase I | Antibodies |
| Ubiquitination | E1, E2, E3 | Ubiquitin (Hochstrasser et al. Annu. Rev. Genet. 1996 30: 405-439) | Lysine | EGPRDGLKKERLLDDRH (SEQ ID No. 31) domain (NP-065390) of IkBa MCSSSANKENDNGNLVD (SEQ ID No. 32) domain (NP-001781) of CDC25C | Antibodies (Fujimuro M et al. FEBS Letts 1994, 349: 173-180.) |
| Proteolysis | Proteases | — | the two amino acids situated at the level of the cleavage site | W/LEHD-X (SEQ ID No. 33) domain recognized by the Caspases 1, 4, 5 DEXD-X (SEQ ID No. 34) domain recognized by the Caspases 2, 3, 7 I/L/VEXD-X (SEQ ID No. 35) domain recognized by the Caspases 6, 8, 9 PFEEKR-X (SEQ ID No. 36) domain recognized by the complement C1r K-X and R-X domains recognized by the trypsin | Antibodies specific to the N or C terminal end of the substrate generated by the cleavage |

IX. DETECTION OF POST-TRANSLATIONAL MODIFICATION MODULATING COMPOUNDS

The method according to the invention is particularly useful for testing the ability of certain so-called "candidate" compounds to modulate post-translational modifications. For this purpose, the detection method according to the invention is implemented in the presence and in the absence of such compounds and the signals obtained are compared. These signals can also be compared with the signals obtained by incubating the cells with known modulators—inhibitors or activators.

The compounds which are potentially modulators of post-translational modifications can act according to several mechanisms:
- allosteric inhibitors, binding to the enzyme;
- competition with a co-factor involved in the enzymatic reaction, for example with a fluorescent donor compound of a group transferred to the protein substrate in the case of the post-translational modifications involving a group transfer. Example: ATP in phosphorylation;
- inhibition of the expression of the enzyme, visible only if the co-factor is present at physiological concentrations;
- activation of an enzyme degradation mechanism, visible only if the enzyme is present at physiological concentrations;
- mechanism which is unknown but resulting in an inhibition, reduction or increase in the signal corresponding to the modified protein substrate.

The method according to the invention makes it possible to exclude the "non-physiological" false positives obtained during the implementation of the in vitro technique of the prior art: these compounds are those which have an effect in vitro but are, in fact, incapable of reaching their target under physiological conditions.

X. Cells Suited to the Implementation of the Method According to the Invention Another aspect of the invention relates to a cell suited to the study of a post-translational modification as described previously characterized in that it comprises:
a) an expression vector coding for a fusion protein comprising the protein substrate and one or two coupling domains; and
b) an expression vector comprising the nucleic acid sequence coding for the enzyme catalyzing said post-translational modification and/or the nucleic acid sequence coding for a protein involved in the activation cascade leading to the post-translational modification, such as a membrane receptor or an enzyme catalyzing the production of an intracellular messenger.

According to a preferred aspect, the cell according to the invention is characterized in that said expression vectors are integrated into the cellular DNA.

The cell according to the invention is, preferably, an immortalized cell.

The cell according to the invention can be of any kind. It is preferably a mammal cell, in particular a human cell.

XI. EXAMPLES

Summary Description

Brief Description of the Drawings

FIG. 4: Comparison of the measurement of the phosphorylated protein substrate by the two approaches (reading in separate wells or reading in a single well)

FIG. 5: Comparison of the measurement of the total protein substrate by the two approaches (reading in separate wells or reading in a single well)

FIG. 6: Ratio of phosphorylated protein substrate: total protein substrate. Meaning of the abbreviation DF: Delta F.

FIG. 7: Inhibition of the activity of the kinase by staurosporine.

Detection of the phosphorylated substrate by using either the antibody STK-europium cryptate as donor compound and anti-Flag-XL665 as FRET acceptor compound, or the antibody STK-europium cryptate as donor compound and a suicide enzyme SNAPTAG and increasing concentrations of its substrate Benzyl Guanine (BG) conjugated to the fluorescent acceptor compound Dy647.

Figure 10:
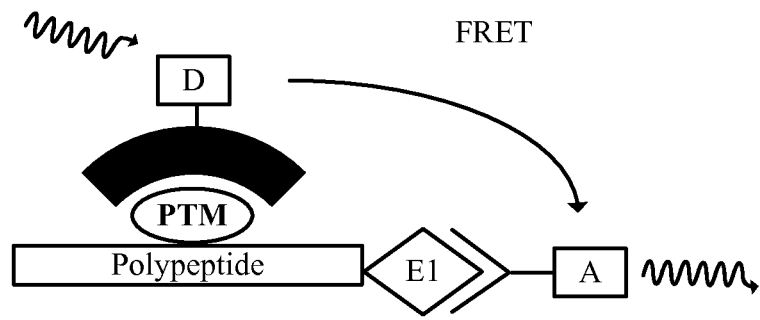
Figure 11A:
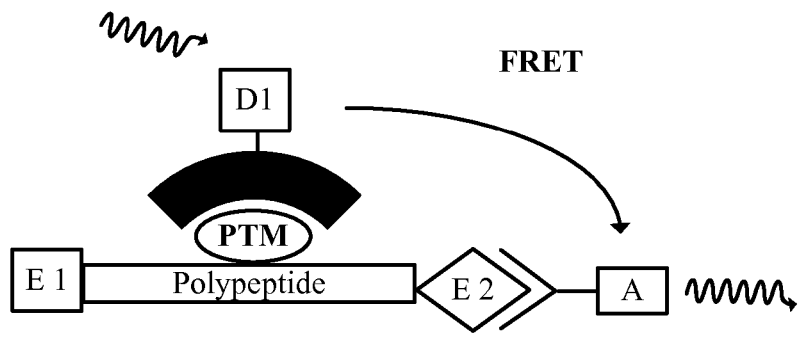
Figure 11A:
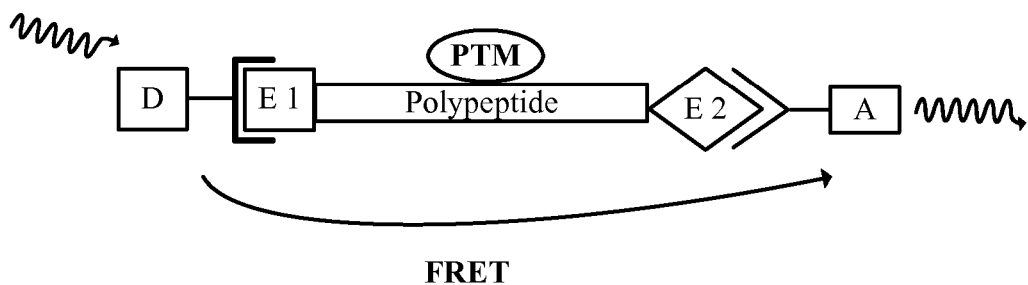
Figure 11B:
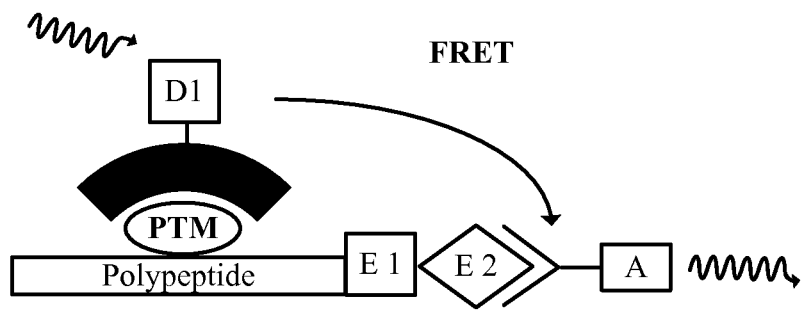
Figure 11B:
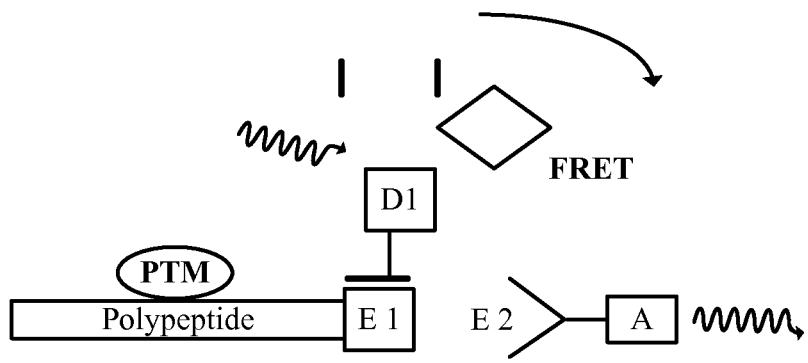
Figure 12:
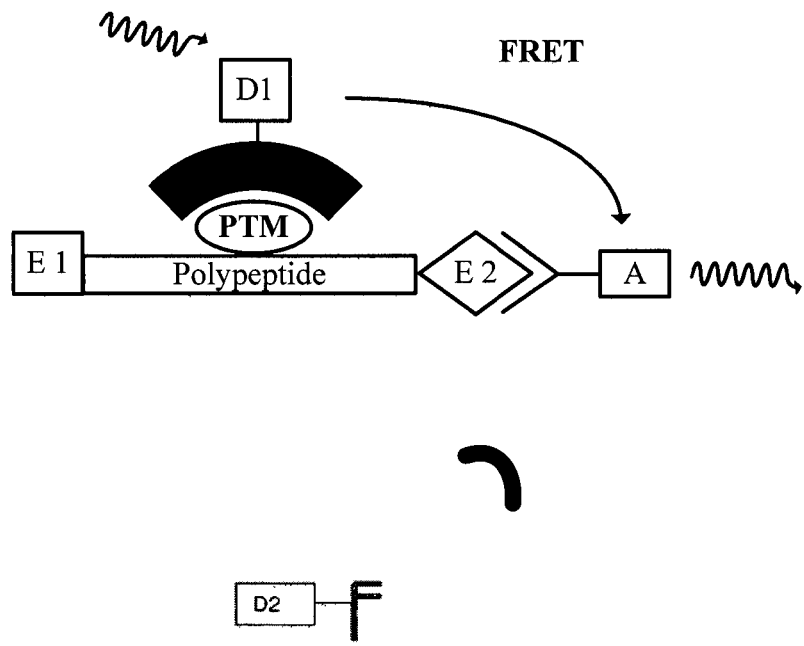
Figure 12:
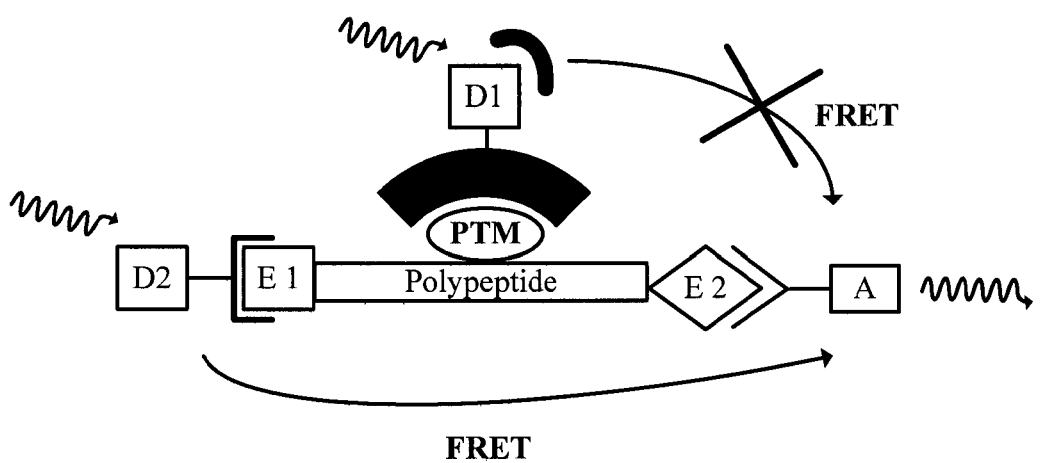

1: Flag-XL665
2: BG-Dy647 3.12 nM (final)
3: BG-Dy647 6.25 nMf
4: BG-Dy647 12.5 nMf
5: BG-Dy647 25 nMf
6: BG-Dy647 50 nMf
7: BG-Dy647 100 nMf FIG. 10: Simple detection of a post-translation modification.
PTM=post-translational modification
E1=1$^{st}$ coupling domain
Pair of FRET partners, Acceptor fluorescent compound/Donor fluorescent compound=A/D
Polypeptide=protein substrate FIG. 11: Detection of the protein substrate having undergone a post-translational modification and detection of the total protein substrate in two different measurement media
11A: tags are not contiguous
11B: tags are contiguous FIG. 12: Detection of the protein substrate having undergone a post-translational modification and detection of the total protein substrate in a single measurement medium (FRET Killer)

Figure 13:
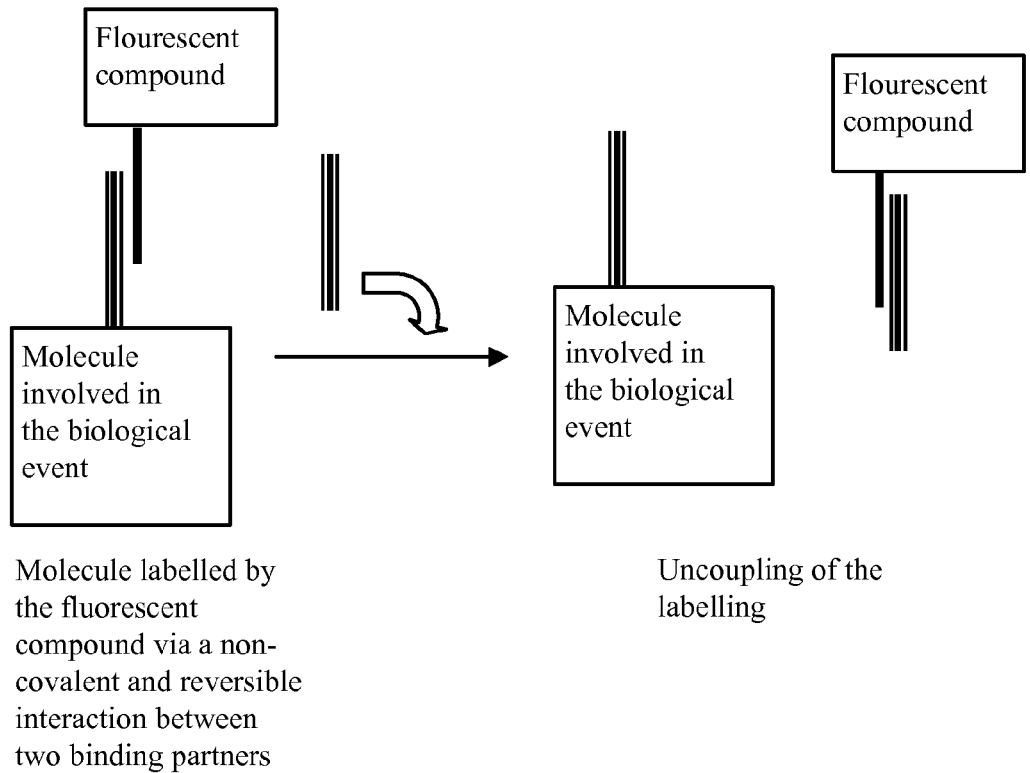

FIG. 13: competition phenomenon

EXAMPLE 1

Measurement of the Phosphorylation of an Akt Protein Substrate by This Enzyme, Transfection of the Protein Substrate Alone or Co-Transfection of the Protein Substrate and the Enzyme This example illustrates the use of the method described in the invention for measuring the phosphorylation of a protein substrate by a homogeneous TR-FRET technique. This example also underlines the importance of the co-transfection of the cells with a plasmid coding for an enzyme inducing a post-translational modification, and with a target peptide sequence.
Protocol
Preparation of the Plasmid Coding for the Substrate:

The following sequence represents the sense strand (5'-3') coding for a fusion protein comprising: the c-myc tag (underlined), a generic substrate recognized by the serine/threonine kinases (in bold), and the FLAG tag (dotted underlining), flanked in position 5' by part of the restriction site of BamH1 and in position 3' by part of the restriction site of Xho1:

(SEQ ID No. 1)
GATCCGAACAAAAACTCATCTCAGAAGAGGATCTGAAGAAGCTCAATCGT

ACGCTGAGCTTCGCAGAGCCTGGCGACTACAAGGACGACGATGACAAGTA

GC

The double-strand oligonucleotide is obtained by hybridizing the following two oligomers:

Sense:
(SEQ ID No. 1)
GATCCGAACAAAAACTCATCTCAGAAGAGGATCTGAAGAAGCTCAATCGT

ACGCTGAGCTTCGCAGAGCCTGGCGACTACAAGGACGACGATGACAAGTA

GC

Antisense:
(SEQ ID No. 2)
TCGAGCTACTTGTCATCGTCGTCCTTGTAGTCGCCAGGCTCTGCGAAGTC

CAGCGTACGATTGAGCTTCTTCAGATCCTCTTCTGAGATGAGTTTTTGTT

CG and by carrying out a PCR reaction with the programme: 95° C. for 10 min/90° C., 5 min/85° C., 5 min/80° C. 15 min/75° C. 60 min/70° C. 15 min/65° C. 10 min/60° C. 5 min/55° C., 5 min/50 min/45° C. 5 min/35° C. 10 min/25° C. 15 min/15° C. 5 min/4° C.

The sequence is inserted into the pSEMS plasmid (from Covalys) by mixing 1 µl of Quick T4 DNA ligase (New England Biolabs Cat No. M2200S), 1 µl of hybridized oligonucleotides and 50 ng of plasmid previously digested with the restriction enzymes BamH1 and Xho1 for 10 min at ambient temperature.

The plasmid is then incubated with One Shot® TOP10 competent cells (Invitrogen Corp. Cat No. C4040-06) for 1 hour at 37° C. then the cells are plated on plates containing ampicillin.

After 1 night at 37° C., 6 colonies are selected, amplified and their identity is confirmed by sequencing.

Transfection of the Cells:

8000 HEK293 cells (ATCC) are either transfected with increasing quantities of plasmid coding for the substrate alone, or co-transfected with the same quantities of plasmid coding for the substrate and 25 ng of Akt1-pcDNA 3.1 (Invitrogen Corp. Cat No. V790-20) The co-transfection is carried out in the presence of Lipofectamine 2000 (Invitrogen corp. Cat No. 11668-019) and OPTI-MEM medium (Gibco Cat No. 31985).

The cells are then cultured for 48 hours at 37° C. in 25 µl of DMEM medium (Gibco Cat No. 11965-092), to which 10% FCS (Hyclone Cat No. SV30014-03) and 1% antibiotic and antifungal (Gibco Cat No. 15240-062) are added in 384-well plates (Proxiplate 384, Perkin-Elmer Cat No. 6006280).

The cells are lysed in 50 mM Hepes buffer, pH7, containing 0.1% BSA, 20 mM EDTA, 0.8 M potassium fluoride and 2% TRITON X-100® (octylphenol ethyelene oxide condensate)). This same buffer contains 1.8 ng of phosphospecific antibodies (STK antibody, Upstate Cat No. 35-002) conjugated with the donor (europium cryptate) and 40 ng of anti-FLAG conjugated with the acceptor (cross-linked allophycocyanin, XL 665, CIS bio international Cat No. 61 FG2XLA).

The plate is incubated for 1 hour at ambient temperature before time-resolved reading.

Analysis of the TR-FRET Signal:

The FRET signals are measured on an Acquest 384 fluorimeter (Molecular Device) in TR-FRET mode at 620 nm (emission wavelength of rare earth cryptate) and 665 nm (emission wavelength of allophycocyanin) after excitation by a flash lamp with a bandwidth comprised between 330 and 380 nm. The ratio between the fluorescence emitted at 665 nm (fluorescence of the acceptor) and the fluorescence emitted at 620 nm (fluorescence of the donor) (Ratio 665/620) represents the FRET occurring between the donor (europium cryptate) and the acceptor (Allophycocyanin). This FRET is proportional to the spatial proximity between the donor and the acceptor.

The delta F (%) (DF) corresponds to:

$$\frac{(\text{Ratio } 665/620 \text{ of the sample} \times 10000) - (\text{Ratio } 665/620 \text{ of the negative control} \times 10000)}{(\text{Ratio } 665/620 \text{ of the negative control} \times 10000)} \times 100$$

The negative control signal corresponds to the signal obtained with the non-transfected cells.

Results

The cells are transfected with the plasmid coding for the substrate alone or co-transfected with this same plasmid coding for the substrate and a plasmid coding for Akt1. After lysis of the cells, the phosphorylation of the substrate is detected using a phosphospecific antibody coupled with europium cryptate (donor) (Ref. CIS biointernational, standard tris bipy extinguished by the FRET killer), and an anti-FLAG antibody coupled with allophycocyanin (Ref. XL665 CIS bio international). The FRET measured is proportional to the spatial proximity between the donor and the acceptor. This proximity results from the fixing/binding of the phosphospecific antibodies to the phosphorylated protein substrate and from the fixing/binding of the anti-FLAG to the FLAG sequence.

Figure 1:
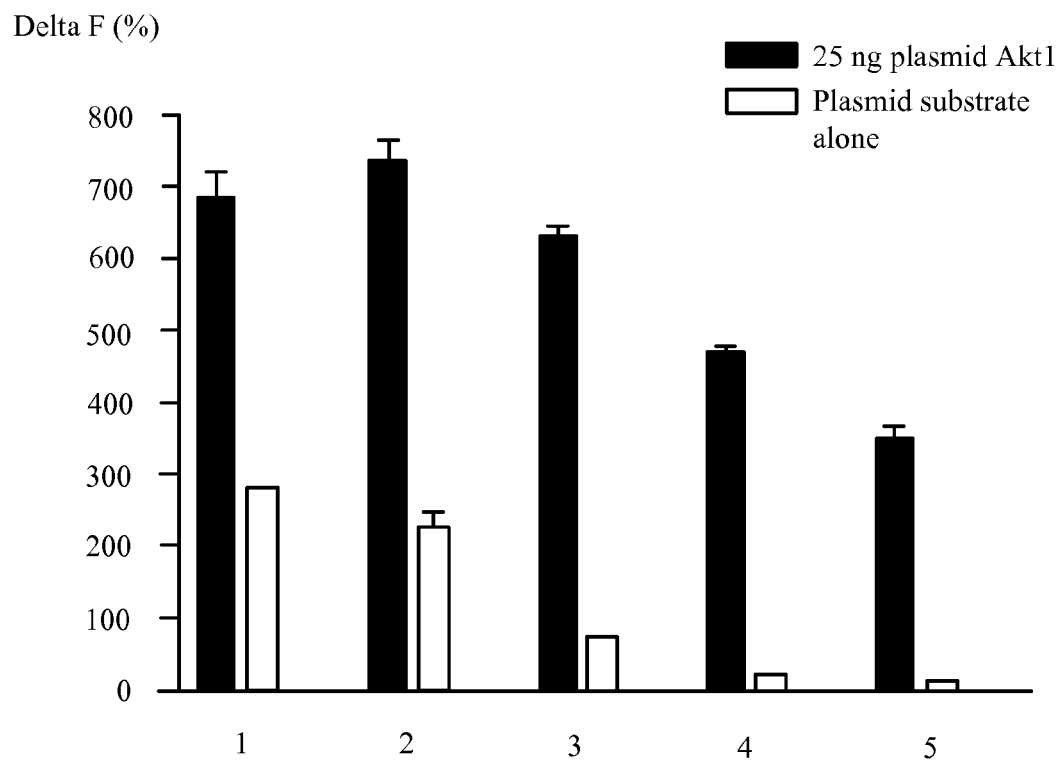
FIG. 1: Co-transfection of Akt1 and a peptide substrate. Measurement of the phosphorylation of the substrate by TR-FRET. Meaning of the abbreviations: plasm.=plasmid Plasm. Sub=plasmid substrate=plasmid coding for the substrate.
1: Plasmid Substrate 25 ng
2: Plasmid Substrate 12.5 ng
3: Plasmid Substrate 6.25 ng
4: Plasmid Substrate 3.12 ng
5: Plasmid Substrate 1.56 ng

FIG. 1 confirms that the FRET measured is proportional to the quantity of phosphorylated protein substrate and therefore that the method according to the invention makes it possible to detect the phosphorylation of a protein substrate by the kinase Akt1, this phosphorylation having taken place in the intracellular membrane.

In the cell, the same protein substrate can in general be phosphorylated by several kinases. The co-transfection of the kinase and its substrate makes it possible to detect the contribution of this particular kinase to the phosphorylation of the protein substrate, and thus to study the effect of (potentially inhibiting) compounds on this kinase.

FIG. 1 shows that when the cell is transfected by the only plasmid coding for the protein substrate, the protein substrate is phosphorylated by the endogenous kinases, including Akt1. The co-transfection with the plasmid coding for the protein substrate and the plasmid coding for the kinase Akt1 makes it possible to increase the quantity of protein substrate phosphorylated specifically by Akt1.

Example 2

Measurement of the Phosphorylation of a Generic Protein Substrate by Cam Kinase II, a Non-Constitutively Active Kinase, in the Presence and in the Absence of Ionomycin Under cell conditions, a kinase is not permanently active, even if the molecules of a population of kinase can be at different levels of activation. This is the case with the Cam kinase II studied in this example, which is here activated by the addition of ionomycin to the medium. This example shows that the method according to the invention can be used with success to detect an intracellular modification (here, phosphorylation of a protein substrate by the Cam kinase II) resulting from an extracellular stimulation (here, chemical stimulation by ionomycin).

Protocol 8000 cells HEK293 are either transfected with increasing quantities of plasmid coding for the substrate alone (Identical to Example 1), or co-transfected with the same quantities of plasmid coding for the substrate and 25 ng of CamKII 6-pcDNA 3.1 (plasmid coding for Cam kinase II). The transfection is carried out as described in Example 1.

The cells are then cultured for 48 hours at 37° C. in DMEM medium, comprising 10% fcetal calf serum and 1% antibiotic and antifungal, then for 16 hours in the same medium without serum.

The cells are stimulated for 5 min in the presence of ionomycin 1 µM (Sigma), and lysed as described above.

The phosphorylation of the protein substrate is detected as described in Example 1.

Results

Figure 2:
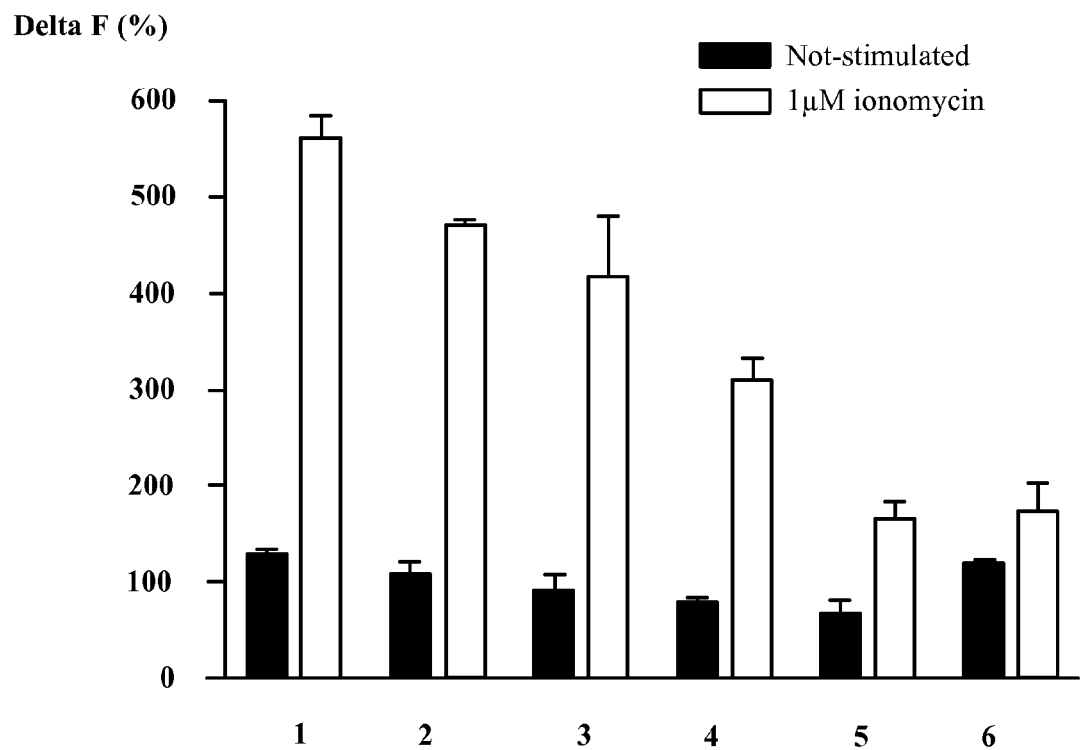
FIG. 2: Co-transfection of CamKII delta and a peptide substrate. Measurement of the phosphorylation of the substrate by TR-FRET after activation of CamKII delta by ionomycin. Meaning of the abbreviations:
CamKIId=plasmid CamKII δ-pcDNA 3.1
1: 50 ng plasmid substrate/50 ng CamKIId
2: 25 ng plasmid substrate/50 ng CamKIId
3: 12.5 ng plasmid substrate/50 ng CamKIId
4: 6.25 ng plasmid substrate/50 ng CamKIId
5: 3.12 ng plasmid substrate/50 ng CamKIId
6: 50 ng plasmid substrate alone

FIG. 2 shows that in the absence of stimulation by ionomycin, the method according to the invention does not make it possible to detect phosphorylated protein substrate, whatever the quantity of plasmid coding for the protein substrate present in the cell.

On the other hand, in the presence of ionomycin, the signal measured is much greater than in its absence. Moreover, this signal is positively correlated with the quantity of plasmid coding for the transfected substrate in the cell.

In order to detect compounds capable of activating Cam kinase II, the ionomycin can be replaced with a compound to be tested and the signals obtained in the absence and in the presence of this compound can be compared.

Certain inhibitor compounds, in particular the allosteric inhibitors, become fixed/bound to the inactive kinase and stabilize it in this state. These same compounds have little or no activity on the kinase when it is active. The method according to the invention makes it possible, by adding a compound to be tested (potential allosteric inhibitor) to the measurement medium before the addition of ionomycin, to detect such allosteric inhibitors.

Example 3

Detection of the Inhibition by Staurosporine of the Phosphorylation of a Generic Protein Substrate by Akt1: Parallel Measurements of the Phosphorylated Protein Substrate and the Total Protein Substrate in 2 Different Wells Example 3 shows that the method of the invention makes it possible to test the ability of a compound to inhibit a kinase.

Protocol

The cells are co-transfected and cultured as described in Example 1. After culture for 48 hours, they are incubated for 1 hour in the presence of increasing concentrations of staurosporine, a known kinase Akt1 inhibitor. The cells are then lysed and the phosphorylated protein substrate detected as described in Example 1.

In parallel, in a second well, cells are treated in identical manner. After lysis, the total quantity of protein substrate is measured using an anti-c-myc antibody coupled with europium cryptate (2.9 ng/well) (CIS bio international Cat No. 61MYCKLA) and an anti-FLAG antibody coupled with allophycocyanin (40 ng/well).

Results

The peptide sequence target is inserted between two peptide sequence tags (c-myc and FLAG). The expressed quantity of these two sequences is therefore equivalent to the expressed quantity of protein substrate. The measurement of the FRET occurring between ac-myc antibody coupled with a donor and an anti-FLAG antibody coupled with an acceptor therefore represents the total quantity of protein substrate expressed by the cell.

Figure 3:
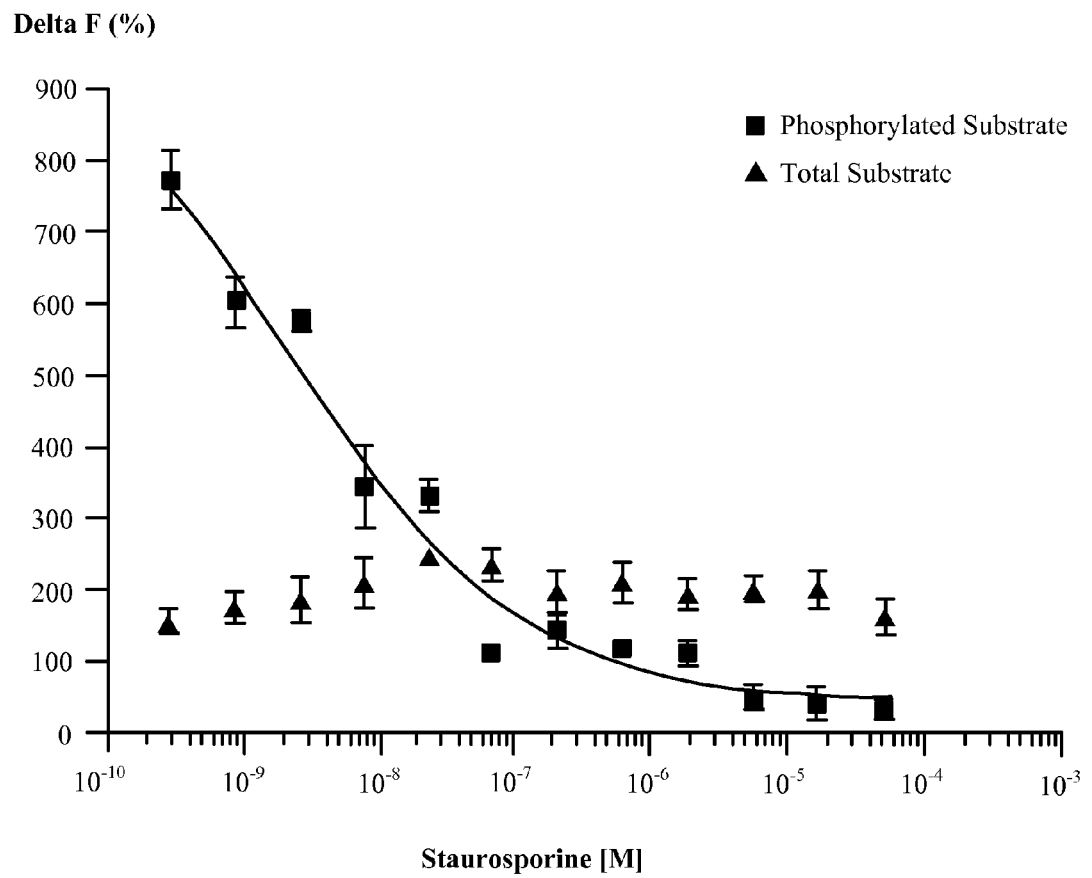
FIG. 3: Inhibition of phosphorylation by staurosporine. Measurement of the quantity of phosphorylated protein substrate and measurement of the total quantity of protein substrate.

FIG. 3 shows, in two separate wells, for each concentration of staurosporine, respectively the measurement of the signal corresponding to the phosphorylated protein substrate, and the measurement of the signal corresponding to the total protein substrate. It is noted that the signal corresponding to the phosphorylated protein substrate reduces with increasing concentrations of Akt1 inhibitor, since the signal corresponding to the total protein substrate remains constant whatever the dose of inhibitor.

The method according to the invention therefore makes it possible to assert that the reduction in the signal corresponding to the phosphorylated protein substrate is linked to the action of the inhibitor and not to a reduction in the quantity of protein substrate expressed in the cell.

Moreover, if the staurosporine is replaced by a compound to be tested, the method according to the invention makes it possible to detect an inhibitor of the post-translational modification studied (here phosphorylation by Akt1).

Example 4

Example 4 is an illustration of the method according to the invention which allows the detection of the protein substrate having undergone a post-translational modification and the detection of the total protein substrate in a single measurement medium (FRET killer).

Figure 4:
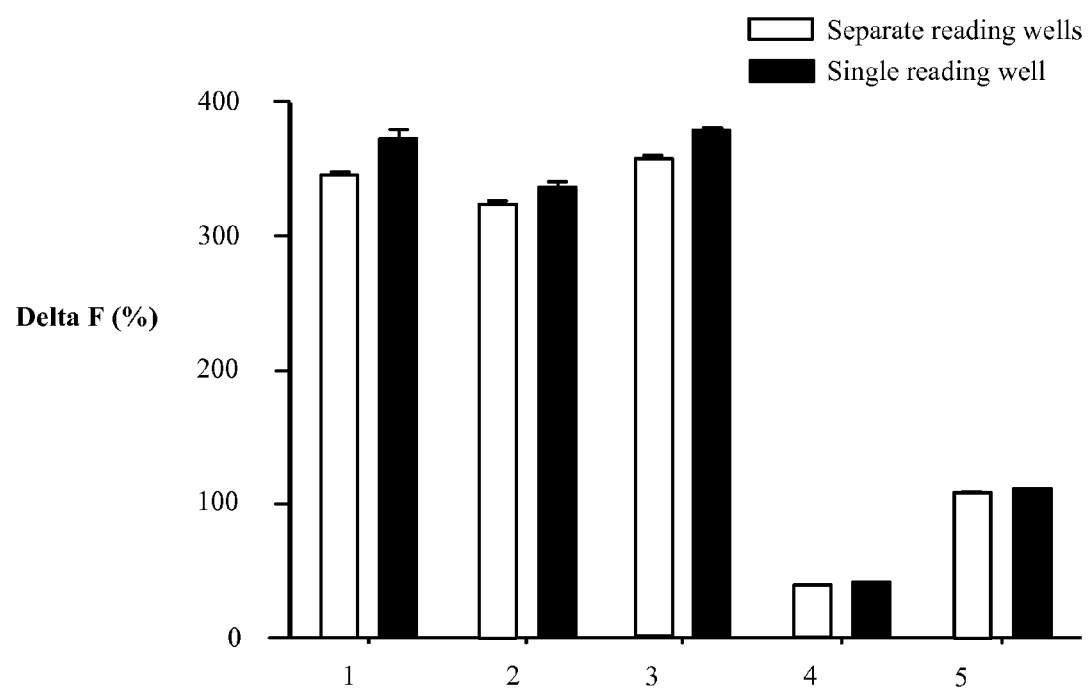
FIGS. 4-7: Measurement of the quantity of phosphorylated protein substrate and the total quantity of protein substrate. Measurement in two separate wells, or measurement of the two parameters in a single well using a FRET suppressing agent.
1: No inhibitor
2: Staurosporine 0.2 nM
3: Staurosporine 20 nM
4: Staurosporine 2 μM
5: Akt DN
Figure 5:
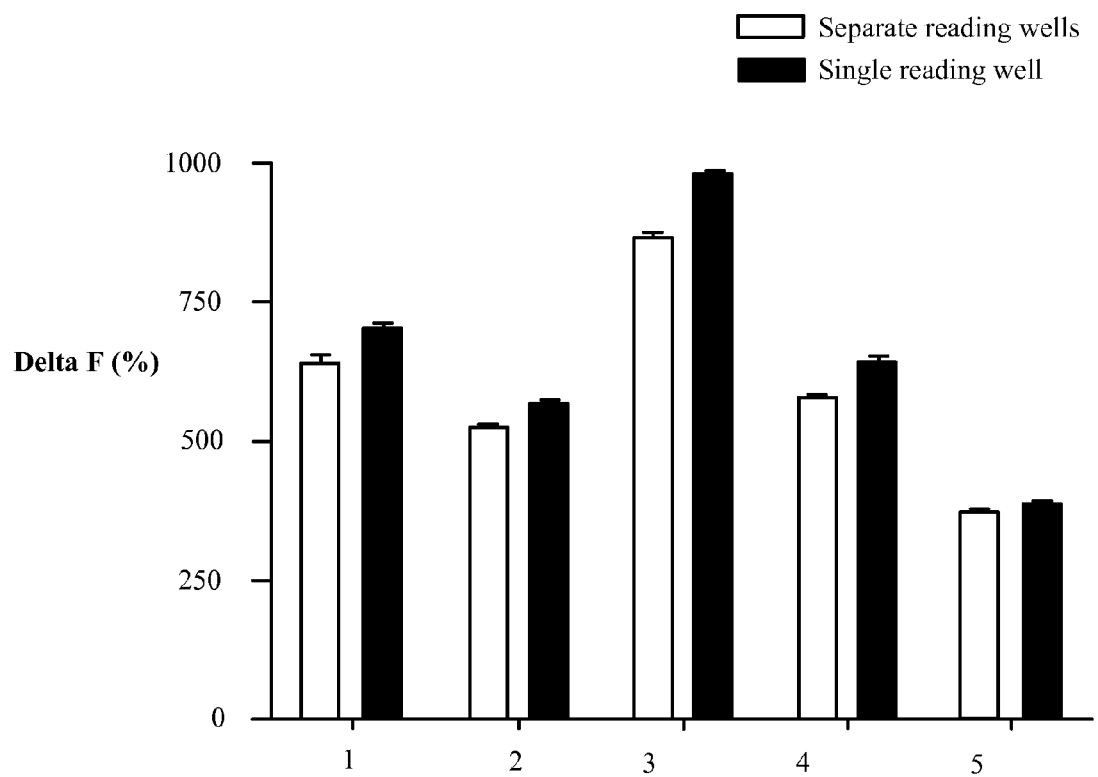

FIGS. 4 and 5 show the comparison of the measurement of the quantity of phosphorylated protein substrate and total protein substrate, under two measurement conditions: measurement carried out in two different wells, or measurement carried out sequentially, in the same well, using a FRET suppressing agent.

This example also underlines the importance of standardizing the quantity of phosphorylated protein substrate relative to the quantity of total protein substrate.

Protocol

The cells are co-transfected with a plasmid coding for the protein substrate labelled by the c-myc and flag tags and with a plasmid coding for Akt1, as described in Example 1. The cells are then treated as described previously with straurosporine. Measurement of the FRET signals corresponding to the phosphorylated protein substrate and to the total protein substrate is carried out either:

In two separate wells after the lysis step,
In the same well. In this case the lysate is first placed in the presence of a phosphospecific antibody, coupled with tris-bipyridine europium cryptate (CIS bio international, formula below), and an anti-FLAG antibody coupled with allophycocyanin (in the same quantities as those described in Example 1). The plate is incubated for 1 hour at ambient temperature before the measurement of the quantity of phosphorylated protein substrate by TR-FRET.

480 ng of an antibody specific to the tris-bipyridine europium cryptate not recognizing the trisbipyridine pentacid cryptate, (formulae below), capable of blocking the FRET between the phosphospecific antibodies and allophycocyanin, as well as an anti-c-myc antibody coupled with a donor (trisbipyridine pentacid cryptate, 1.1 ng) not sensitive to the FRET suppressing agent and compatible with allophycocyanin are then added to the well. After 1 hour, the signal corresponding to the total protein substrate is measured by TR-FRET.

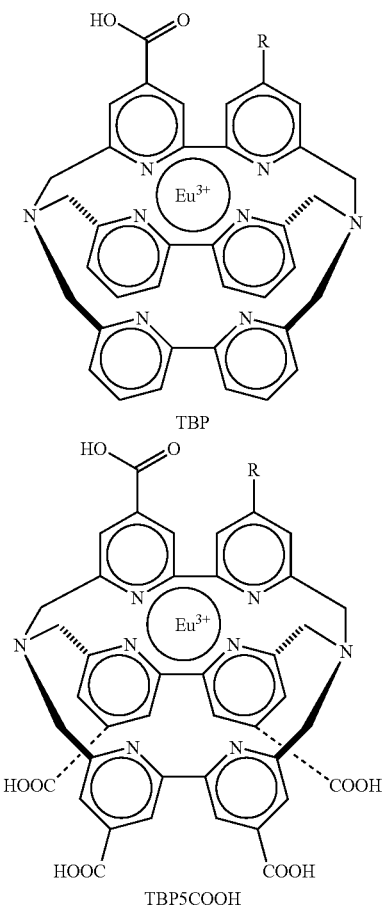

Bis-Bipyrine Europium and Trisbipyridine Pentacid Cryptates

Results

FIGS. 4 and 5 show the results of the measurements of the phosphorylated and total protein substrate according to the two methods. "Akt DN" signifies that the cells have been transfected with a plasmid coding for a negative dominant mutant of Akt, i.e. which does not catalyze by phosphorylation but which is capable of binding to staurosporine.

FIG. 4 shows that, in both cases, a signal corresponding to the phosphorylated protein substrate is measured, and that this signal appears to be sensitive to staurosporine only in the case where it is added to the measurement medium at high concentrations (2 µM).

FIG. 5 shows that in both cases (measurements carried out in the same well or in two separate wells), a signal corresponding to the total protein substrate is measured. It is noted that the signals corresponding to the total protein substrate vary from one well to the other. In particular, the wells into which 20 nM of staurosporine have been introduced in fact contain far more protein substrate than the other wells.

Figure 6:
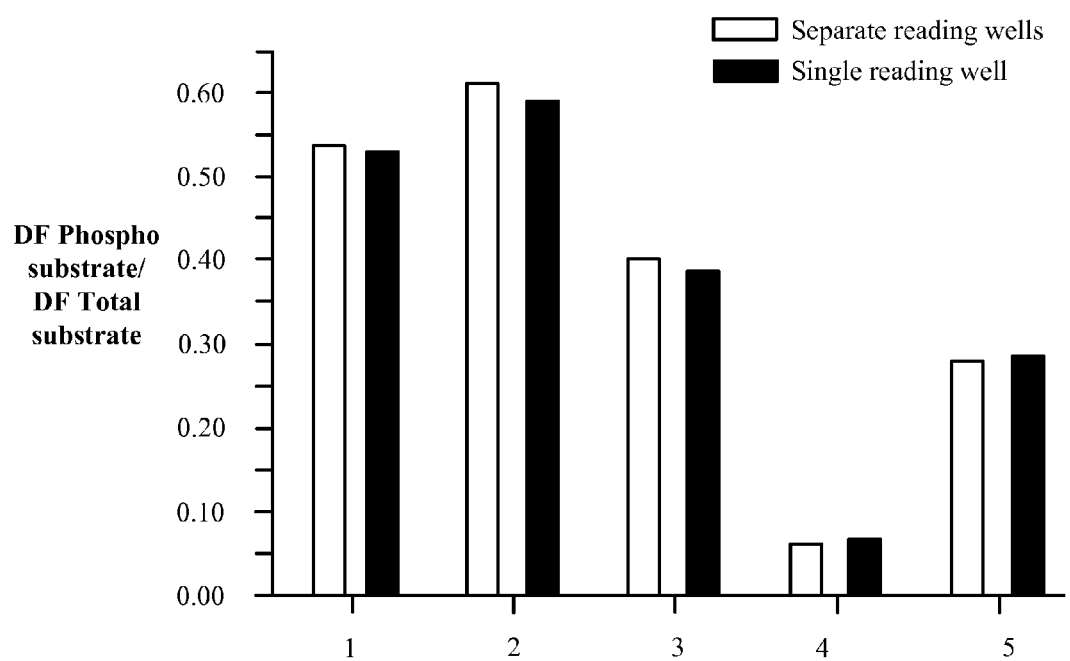

FIG. 6 shows the usefulness of standardizing, for each experimental condition, the signal corresponding to the phosphorylated protein substrate by the signal corresponding to the total protein substrate, in order to be rid of the inter-well variations which mask, for example, the effect of 20 nM staurosporine in FIG. 4. FIG. 6 thus demonstrates the inhibition of the phosphorylation of the protein substrate by staurosporine, much more precisely than in FIG. 4.

In order to have an exact idea of the quantity of modified protein substrate in a cell, it is therefore necessary to relate this quantity of modified protein substrate to the total quantity of protein substrate contained in the same sample.

Figure 7:
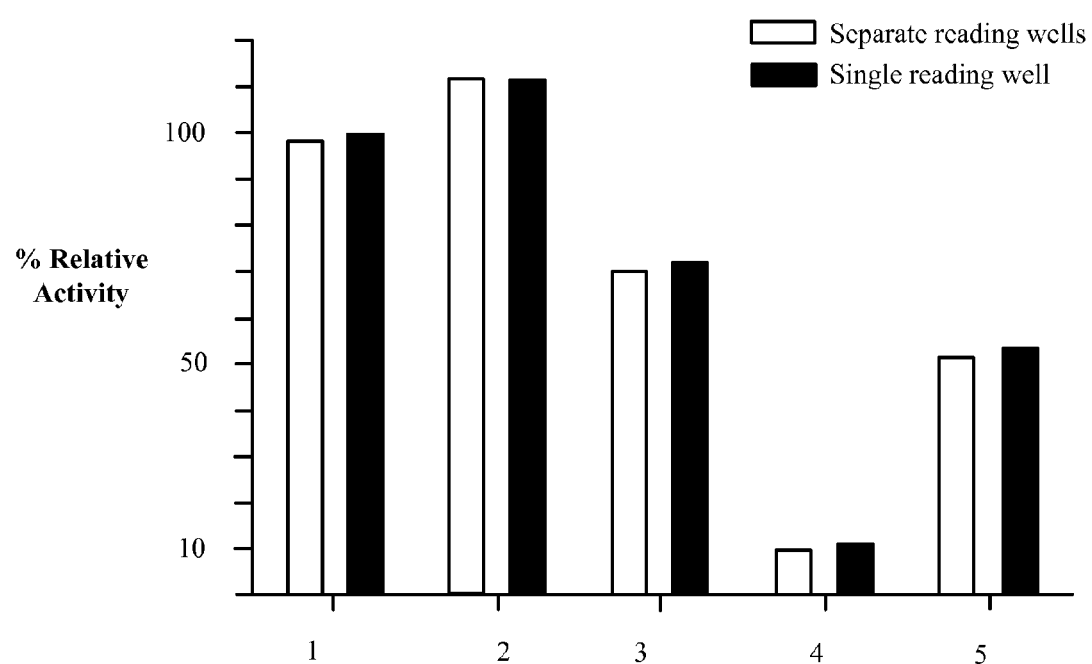

In FIG. 7, the signal corresponding to the activity of the kinase is standardized with respect to the signal corresponding to the activity of the kinase in the absence of inhibitor. This makes it possible to approximately evaluate the 1050 value of staurosporine for Akt1.

Example 5

Use of Covalent Labelling Using O(6)-Alkylguanine-DNA Alkyltransferase (SNAPTAG) Activity to Measure the Expression and Phosphorylation of an Akt Protein Substrate by Co-Transfection of the Protein Substrate and of the Enzyme This example illustrates the use of the method according to the invention for measuring the level of phosphorylation and the quantity of substrate expressed after co-transfection in the cells of the plasmid coding for the protein substrate and of the plasmid coding for the Akt kinase.

This example illustrates in particular the use of a suicide enzyme as a coupling domain, in this case O(6)-alkylguanine-DNA alkyltransferase (SNAPTAG), for labelling the substrate with a coupling agent, in this case a Benzylguanine-Dy647 conjugate as a fluorescent acceptor compound. This implementation is an excellent alternative to the use of tag/antitag systems for labelling the substrate by one of the FRET partner components, in this case the Dy647 acceptor.

Protocol

Preparation of the Plasmid Coding for the Substrate:

The following sequence represents the sense strand (5'-3') coding for a fusion protein comprising: the c-myc tag (underlined), a generic substrate recognized by the serine/threonine kinases (in bold) and the FLAG tag (dotted underlining), flanked in position 5' by part of the restriction site of BamH1 and in position 3' by part of the restriction site of Xho1:

(SEQ ID No. 1)
GATCCGAACAAAAACTCATCTCAGAAGAGGATCTGAAGAAGCTCAATCGT

ACGCTGAGCTTCGCAGAGCCTGGCGACTACAAGGACGACGATGACAAGTA

GC

The double-strand oligonucleotide is obtained by hybridizing the following two oligomers:

Sense:
(SEQ ID No. 1)
GATCCGAACAAAAACTCATCTCAGAAGAGGATCTGAAGAAGCTCAATCGT

ACGCTGAGCTTCGCAGAGCCTGGCGACTACAAGGACGACGATGACAAGTA

GC

Antisense:
((SEQ ID No. 2)
TCGAGCTACTTGTCATCGTCGTCCTTGTAGTCGCCAGGCTCTGCGAAGTC

CAGCGTACGATTGAGCTTCTTCAGATCCTCTTCTGAGATGAGTTTTTGTT

CG and by carrying out a PCR reaction with the programme: 95° C. for 10 min/90° C., 5 min/85° C., 5 min/80° C. 15 min/75° C. 60 min/70° C. 15 min/65° C. 10 min/60° C. 5 min/55° C., 5 min/50 min/45° C. 5 min/35° C. 10 min/25° C. 15 min/15° C. 5 min/4° C.

The sequence is inserted into the pSEMS plasmid (from Covalys) by mixing 1 µl of Quick T4 DNA ligase (New England Biolabs Cat No. M2200S), 1 µl of hybridized oligonucleotides and 50 ng of plasmid previously digested with the restriction enzymes BamH1 and Xho1 for 10 min at ambient temperature.

The plasmid is then incubated with One Shot® TOP10 competent cells (Invitrogen Corp. Cat No. C4040-06) for 1 hour at 37° C. then the cells are plated on plates containing ampicillin.

After 1 night at 37° C., 6 colonies are selected, amplified and their identity is confirmed by sequencing.

Transfection of the Cells:

80000 HEK293 cells (ECACC) are either co-transfected with 31.25 ng of plasmid coding for the substrate and 250 ng Akt1-pcDNA 3.1 (Invitrogen Corp. Cat No. V790-20) or by 280 ng of empty pcDNA3.1 plasmid (Invitrogen Corp. Cat No. V790-20). The co-transfection is carried out in the presence of Lipofectamine 2000 (Invitrogen corp. Cat No. 11668-019) and OPTI-MEM medium (Gibco Cat No. 31985).

The cells are then cultured for 24 h at 37° C. in 100 µl of DMEM medium (Gibco Cat No. 11965-092), to which are added 10% FCS (Hyclone Cat No. SV30014-03) and 1% antibiotic and antifungal (Gibco Cat No. 15240-062) in 96-well assay plates (Cellstar black).

The cells are lysed in 50 mM Hepes buffer, pH 7, containing 0.1% BSA, 0.4 M potassium fluoride, 1 mM de DTT, 1% TRITON X-100® (octylphenol ethyelene oxide condensate), 20 mM EDTA, 1×ser/thre phosphatase inhibitors (sigma) under 50 µl after aspiration of the 150 µl transfection medium. In a 50 mM Hepes buffer pH 7.2 containing 0.1% BSA, 0.4M potassium fluoride, 1 mM DTT the following are added (under 50 µL) 5.4 ng phosphospecific antibodies (STK antibody, Upstate Cat No. 35-002) conjugated with the donor (europium cryptate) and 60 ng anti-FLAG conjugated with the acceptor (cross-linked allophycocyanin XL 665, CIS bio international Cat No. 61FG2XLA) or increasing quantities (3.12 nM to 100 nM) of benzylguanine BG conjugated with the acceptor BG-Dy647 (Dyomics) to measure the level of phosphorylation.

This same buffer contains 5.4 ng anti-c myc antibody (Cisbio CIS bio international Cat No. 61 MYCKLA) conjugated with the donor (europium cryptate) and 60 ng anti-FLAG conjugated with the acceptor (cross-linked allophycocyanin, XL 665, CIS bio international Cat No. 61FG2XLA) or increasing quantities (3.12 nM to 100 nM) of benzylguanine BG conjugated with the acceptor BG-Dy647 (Dyomics GmbH) to measure the level of expression of the substrate.

The plate is incubated for up to 20 h at ambient temperature before time-resolved reading.

Analysis of the TR-FRET Signal:

The FRET signals are measured on a Rubystar at 620 nm (emission wavelength of rare earth cryptate) and 665 nm (emission wavelength of allophycocyanin and DY647) after excitation by a laser at 330 nm. The ratio between the fluorescence emitted at 665 nm (fluorescence of the acceptor) and the fluorescence emitted at 620 nm (fluorescence of the donor) (Ratio 665/620) represents the FRET occurring between the donor (europium cryptate) and the acceptor (Allophycocyanin Dy647). This FRET is proportional to the spatial proximity between the donor and the acceptor.

The delta F (%) (DF) corresponds to:

$$\frac{(\text{Ratio 665/620 of the sample} \times 10000) - (\text{Ratio 665/620 of the negative control} \times 10000)}{(\text{Ratio 665/620 of the negative control} \times 10000)} \times 100$$

The negative control signal corresponds to the signal obtained with the cells transfected by an empty pcDNA3.1 plasmid.

Results

The cells are transfected with the empty plasmid pcDNA3.1 or co-transfected by the plasmids coding for the substrate and the Akt kinase. After lysis of the cells, the level of expression and the phosphorylation of the substrate are detected by using:

Either the antibody pair anti c-myc donor/anti-Flag acceptor or the pair anti c-myc donor/BG-Dy647 as acceptor in order to determine the level of expression of the transfected substrate. (FIG. 8).

Or the antibody pair STK donor anti-Flag acceptor or the pair anti STK donor/BG-Dy647 as acceptor in order to determine the level of phosphorylation of the substrate by the action of the Akt kinase. (FIG. 9).

Figure 8:
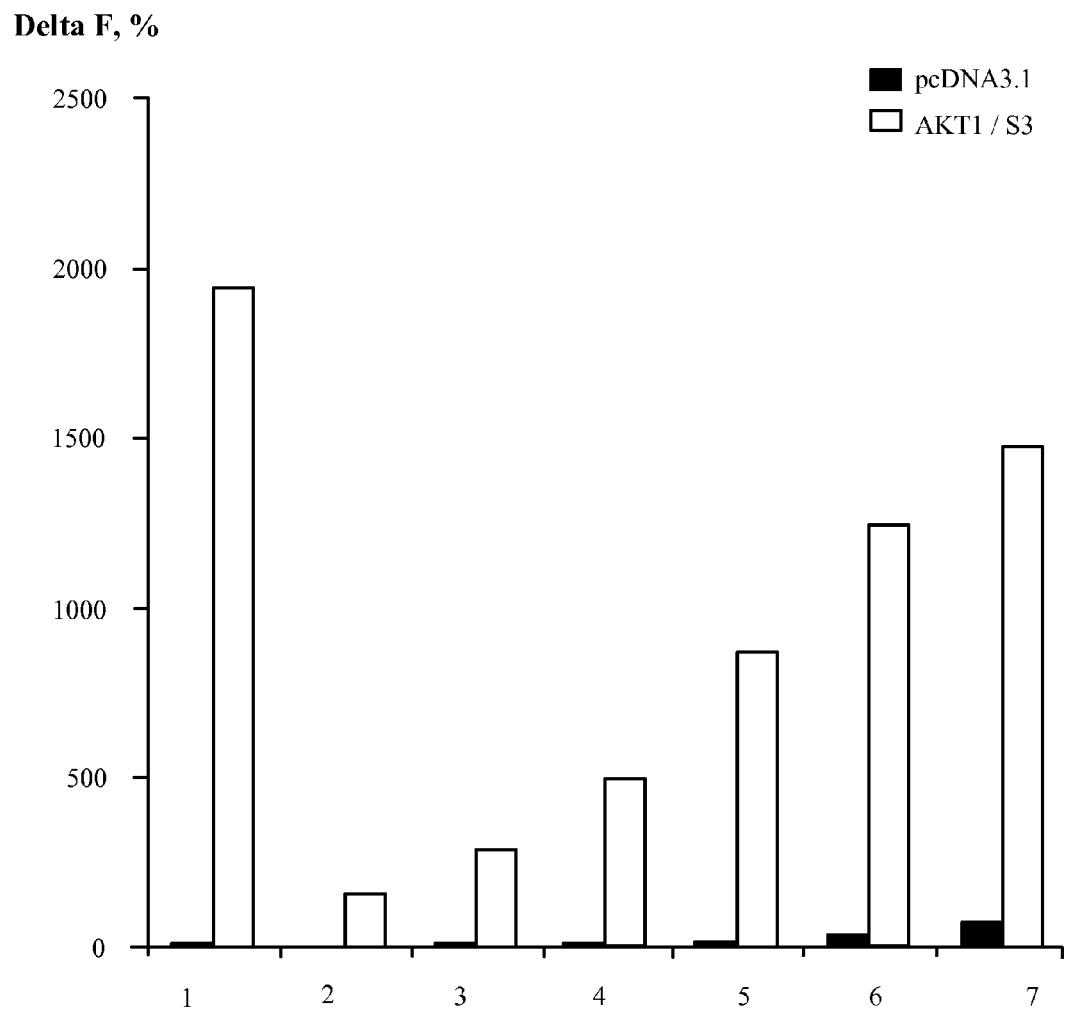
FIG. 8: Co-transfection of Akt kinase and substrate—Measurement of total expressed substrate Detection of the expressed substrate by using either anti c-myc-europium cryptate as donor compound, and anti-Flag-XL665 as FRET acceptor compound, or anti c-myc-europium cryptate and a suicide enzyme SNAPTAG and increasing concentrations of its substrate Benzyl Guanine (BG) conjugated to the fluorescent acceptor compound Dy647.
1: Flag-XL665
2: BG-Dy647 3.12 nM (final)
3: BG-Dy647 6.25 nMf
4: BG-Dy647 12.5 nMf
5: BG-Dy647 25 nMf
6: BG-Dy647 50 nMf
7: BG-Dy647 100 nMf
Figure 9:
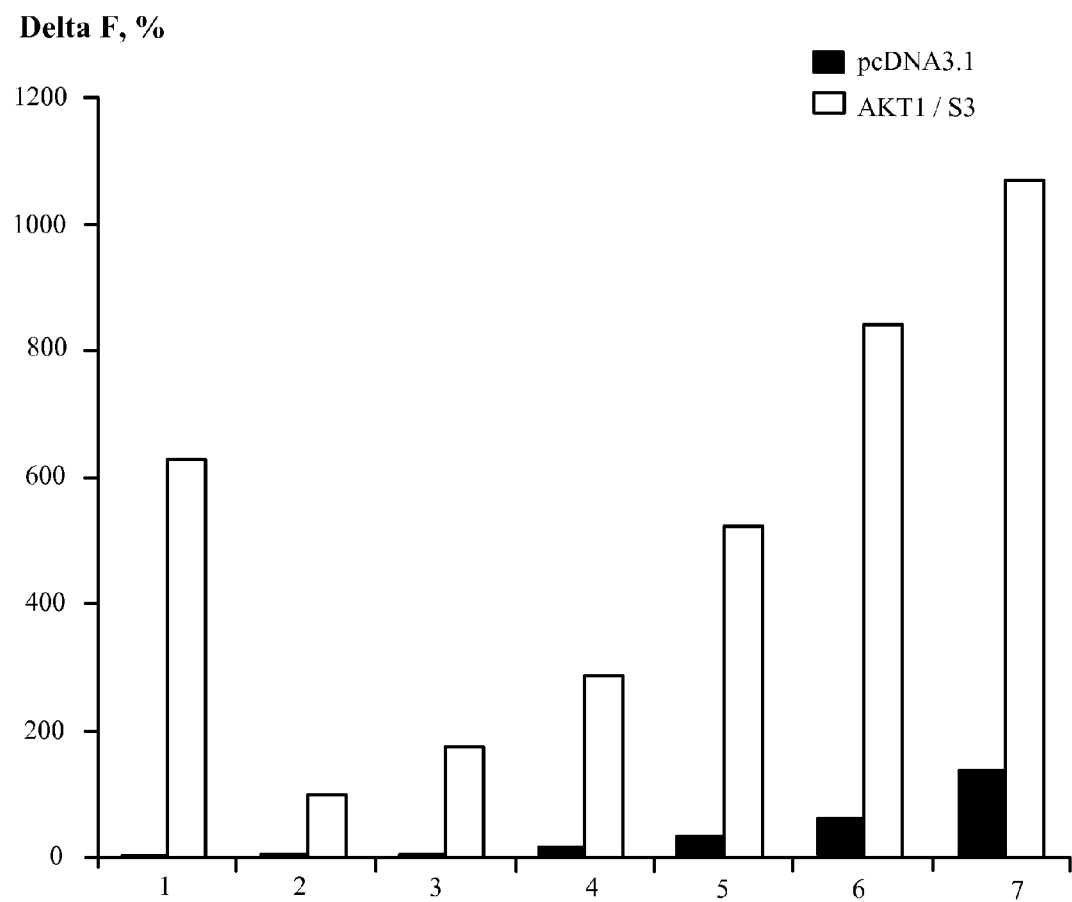
FIG. 9: Co-transfection of Akt kinase and substrate—Measurement of phosphorylated substrate.

The results obtained confirm that a FRET signal is measured between the europium cryptate bonded to the non-phosphorylated substrate via a tag/antitag (-myc) system, and the acceptor Dy647 bonded to the non-phosphorylated substrate via a coupling domain (SNAPTAG suicide enzyme), and this signal is proportional to the quantity of coupling agent BG-Dy647 (FIG. 8).

a FRET signal is also measured between the europium cryptate bonded to the non-phosphorylated substrate via an anti-STK antibody and the acceptor Dy647 bonded to the substrate via a coupling domain (SNAPTAG suicide enzyme), and this signal is proportional to the quantity of coupling agent BG-Dy647 (FIG. 9).

This example demonstrates that the labelling of the substrate (whether or not it has undergone a post-translational modification) can be carried out equally well with tag/anti-tag systems or by suicide enzymes of the SNAPTAG type.

---

The invention claimed is:

1. A method for detection in a homogeneous medium of a post-translational modification of a protein or peptide substrate catalyzed by a cell enzyme, wherein the post-translational modification is a reaction that takes place in intact living cells, wherein the cells comprise a heterologous expression vector coding for a fusion protein comprising the protein or peptide substrate and a first coupling domain, wherein the fusion protein also comprises a second coupling domain, different from the first coupling domain, said second coupling domain not being affected by the post-translational modification, said method comprising the following steps:

(i) incubating the cells in the presence or in the absence of a compound to be tested capable of modulating the activity of said enzyme;

(ii) distributing the cells incubated during step (i) in two different measurement media first and second measurement media;

(iii) adding to a first measurement medium a first fluorescent compound that is a member of a first pair of FRET (Fluorescence Resonance Energy Transfer) partners, said first fluorescent compound being covalently bonded to a coupling agent capable of binding specifically to said first coupling domain present on the protein or peptide substrate; and said first pair of FRET partners emitting a FRET signal when the FRET partners are close to one another;

(iv) adding to said first measurement medium a second fluorescent compound that is a member of this first pair of FRET partners, said second fluorescent compound being covalently bonded to a binding domain specific to the site of the protein or peptide substrate having undergone the post-translational modification and not binding to the non-modified protein or peptide substrate;

(v) measuring the FRET signal emitted by the first measurement medium, this signal representing the quantity of protein or peptide substrate having undergone said post-translational modification;

(vi) adding to a second measurement medium said first fluorescent compound that is a member of said first pair of FRET partners, said first fluorescent compound being covalently bonded to a coupling agent capable of binding specifically to said first coupling domain present on the protein or peptide substrate;

(vii) adding to said second measurement medium a third fluorescent compound constituting with the first fluorescent compound a second pair of FRET partners, this third fluorescent compound being covalently bonded to a coupling agent capable of binding specifically to said second coupling domain, and said second pair of FRET partners emitting a FRET signal when the FRET partners are close to one another;

(viii) measuring the FRET signal emitted by the second measurement medium, this signal representing the total quantity of protein or peptide substrate; and (ix) standardizing the signal measured in step (v) by the signal measured in step (viii), thereby detecting the post-translational modification of the protein or peptide substrate.

2. The method of claim 1, comprising a step of permeabilizing the cells before step (ii) or before step (iii) and/or (vi).

3. The method of claim 1, further comprising a step of comparison of the signals obtained in the presence and in the absence of said compound to be tested, a difference in signal representing the action of the compound to be tested on said post-translational modification.

4. The method of claim 1, wherein the cells also comprise an expression vector comprising a nucleic acid sequence coding for the enzyme catalyzing said post-translational modification, for a protein involved in an activation cascade leading to said post-translational modification, for a membrane receptor or for an enzyme catalyzing the production of an intracellular messenger.

5. The method of claim 1, wherein the post-translational modification is Mono ADP ribosylation; Poly ADP ribosylation; Acetylation; Glutathionylation; O-Glycosylation; N-Glycosylation; Methylation; Nitration; Phosphorylation; Prenylation; Sumoylation; Ubiquitination; or Proteolysis.

6. The method of claim 1, wherein said binding domain specific to the site of the protein or peptide substrate having undergone the post-translational modification is an antibody, an antibody fragment, a protein or nucleic aptamer binding specifically to said site of the protein or peptide substrate having undergone said post-translational modification.

7. The method of claim 1, wherein the first coupling domain and/or the second coupling domain is/are:
(a) a protein tag of 4 to 250 amino acids, glutathione S-transferase, avidin, a peptide constituted by 6 histidines (6-HIS), a peptide constituted by the amino acids 410-419 of the human Myc protein (SEQ ID No. 4), a FLAG peptide of sequence DYKDDDDK (SEQ ID No. 3), an influenza hemagglutinin epitope (HA);
(b) a suicide enzyme or a fragment of a suicide enzyme, O(6)-alkylguanine-DNA alkyltransferase or dehalogenase; or
c) dihydrofolate reductase.

8. The method of claim 7, wherein:
(a) the first or the second coupling domain is a protein tag of 4 to 250 amino acids; and
(b) the first or the second coupling agent is an antibody or an antibody fragment specific to said protein tag.

9. The method of claim 1, wherein the FRET partners are luminescent proteins, green fluorescent protein (GFP) or its variants, fluorescent proteins extracted from corals, phycobiliproteins, B-phycoerythrin, R-phycoerythrin, C-phycocyanin, allophycocyanins, XL665; luminescent organic molecules, rhodamines, cyanines, squaraines, fluorophores, fluoresceins, rare earth cryptates, rare earth chelates, europium, terbium, samarium, dysprosium, neodymium chelates and cryptates; luminescent inorganic particles, or nanocrystals.

10. The method of claim 1, wherein one or several of said first, second or third fluorescent compounds include(s), in addition to a fluorescent compound and a coupling agent or a domain binding to the site of the protein or peptide substrate modified by the post-translational modification, a domain allowing said first, second or third fluorescent compound to pass through the plasma membrane without permeabilization of the latter.

11. The method of claim 10, wherein said domain allowing said first, second or third fluorescent compound to pass through the plasma membrane is esters, pivaloyl-oxymethyl ester, acetoxymethyl ester, glycol esters; viral peptides carried by membrane transporters, penetratin and its analogues, transportan and its analogues, polyarginine groups, peptoids carrying the guanidine groups, oligoguanidinium groups; cholesterol groups, vitamin E or aliphatic chains, undecyl or 1,2-di-O-hexadecyl-glycerol chains.

12. A method for detection in homogeneous medium of a post-translational modification of a protein or peptide substrate catalyzed by a cell enzyme, wherein the post-translational modification is a reaction that takes place in intact living cells, wherein these cells comprise a heterologous expression vector coding for a fusion protein comprising the protein or peptide substrate and a first coupling domain, wherein the fusion protein also comprises a second coupling domain different from the first coupling domain, said second coupling domain not being affected by the post-translational modification, said method comprising the following steps:
(i) incubating the cells in the presence or absence of a compound to be tested capable of modulating the activity of said enzyme,
(ii) adding to a measurement medium a first fluorescent compound that is a member of a first pair of FRET partners, said first fluorescent compound being covalently bonded to a coupling agent capable of binding specifically to said first coupling domain present on the protein or peptide substrate, and said first pair of FRET partners emitting a FRET signal when the FRET partners are close to one another;
(iii) adding to the measurement medium a second fluorescent compound member of this first pair of FRET partners, said second fluorescent compound being covalently bonded to a binding domain specific to the site of the protein or peptide substrate having undergone the post-translational modification and not binding to the non-modified protein or peptide substrate,
(iv) measuring the FRET signal emitted by the first pair of FRET partners, this signal representing the quantity of protein or peptide substrate having undergone said post-translational modification,
(v) adding to the measurement medium an agent suppressing the FRET signal measured in step (iv),
(vi) adding to the measurement medium a third fluorescent compound covalently bonded to a coupling agent capable of binding specifically to said second coupling domain, this third fluorescent compound being compatible with the first fluorescent compound so as to constitute therewith a second pair of FRET partners, the first and the second pair of FRET partners having the same spectroscopic characteristics, and said second pair of FRET partners emitting a FRET signal when the FRET partners are close to one another,
(vii) measuring the FRET signal emitted by the second pair of FRET partners, this signal representing the quantity of total protein or peptide substrate, and
(viii) standardizing the signal measured during step (iv) by that measured during step (vii), thereby detecting the post-translational modification of the protein or peptide substrate.

13. The method of claim 12, comprising a step of permeabilizing the cells placed before step (ii), (iii), (v) and/or (vi).

14. The method of claim 12, wherein the FRET suppressing agent is a compound comprising a binding domain specific to one of the members of the first pair of FRET partners.

15. The method of claim 14, wherein:
(a) the first fluorescent compound is a fluorescent acceptor compound of the first pair of FRET partners,
(b) the second fluorescent compound is a fluorescent donor compound of the first pair of FRET partners,
(c) the third fluorescent compound is a donor compatible with the first fluorescent compound so as to constitute therewith the second pair of FRET partners, and
(d) the FRET suppressing agent is a compound comprising a binding domain specific to the second fluorescent compound, an antibody or an antibody fragment binding to the second fluorescent compound of the first pair of FRET partners.

16. The method of claim 15, wherein the second fluorescent compound is a rare earth cryptate or chelate and the FRET suppressing agent is an antibody or antibody fragment specific to this rare earth cryptate or chelate.

* * * * *

UNITED STATES PATENT AND TRADEMARK OFFICE
CERTIFICATE OF CORRECTION

PATENT NO.       : 8,663,928 B2                                                                 Page 1 of 1
APPLICATION NO.  : 12/516333
DATED            : March 4, 2014
INVENTOR(S)      : Trinquet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 971 days.

Signed and Sealed this

Twenty-ninth Day of September, 2015

Michelle K. Lee
*Director of the United States Patent and Trademark Office*